US012251119B2

(12) United States Patent
Naglreiter et al.

(10) Patent No.: US 12,251,119 B2
(45) Date of Patent: Mar. 18, 2025

(54) ASPIRATION SYSTEMS, DEVICES AND METHODS FOR TREATING ISCHEMIC STROKE

(71) Applicant: POSEYDON MEDICAL, LLC, Miramar, FL (US)

(72) Inventors: Brett E. Naglreiter, Boca Raton, FL (US); Eduardo Ampuero, Miami, FL (US); Alejandro Espinosa, Miami, FL (US)

(73) Assignee: POSEYDON MEDICAL, LLC

( * ) Notice: Subject to any disclaimer, the term of this patent is extended or adjusted under 35 U.S.C. 154(b) by 436 days.

(21) Appl. No.: 17/580,592

(22) Filed: Jan. 20, 2022

(65) Prior Publication Data

US 2022/0168002 A1   Jun. 2, 2022

Related U.S. Application Data

(63) Continuation-in-part of application No. 17/075,805, filed on Oct. 21, 2020, now abandoned.

(60) Provisional application No. 63/277,578, filed on Nov. 9, 2021, provisional application No. 63/235,104, filed on Aug. 19, 2021, provisional application No. 63/232,151, filed on Aug. 11, 2021, provisional application No. 63/173,921, filed on Apr. 12, 2021, provisional application No. 63/173,937, filed on Apr. 12, 2021, provisional application No. 63/173,927, filed on Apr. 12, 2021, provisional application No. 62/949,477, filed on Dec. 18, 2019.

(51) Int. Cl.
*A61B 17/22* (2006.01)
*F04B 43/12* (2006.01)

(52) U.S. Cl.
CPC .......... *A61B 17/22* (2013.01); *F04B 43/1253* (2013.01); *A61B 2017/22079* (2013.01); *A61B 2217/005* (2013.01); *A61B 2217/007* (2013.01)

(58) Field of Classification Search
CPC ....... F04B 43/1253; A61B 2017/00199; A61B 2017/0019; A61B 2017/00154; A61B 2017/00146; A61B 2017/00141
See application file for complete search history.

(56) References Cited

U.S. PATENT DOCUMENTS

| | | | |
|---|---|---|---|
| 3,955,574 A | 5/1976 | Rubenstein | |
| 10,531,883 B1 | 1/2020 | Deville | |
| 11,096,712 B2 | 8/2021 | Teigen | |
| 2007/0060834 A1* | 3/2007 | Odland | A61M 25/0017 600/300 |
| 2012/0138833 A1 | 6/2012 | Matteo | |
| 2017/0056032 A1* | 3/2017 | Look | A61M 1/74 |
| 2017/0238953 A1 | 8/2017 | Yang | |
| 2022/0040394 A1* | 2/2022 | Saroha | A61M 1/743 |

FOREIGN PATENT DOCUMENTS

WO   2014151209   9/2014

* cited by examiner

*Primary Examiner* — Jocelin C Tanner

(57) ABSTRACT

The present invention relates to methods, devices and systems for performing the removal of thrombus from a vessel lumen. More particularly the present invention relates to a thrombectomy system that includes an elongate catheter and a disposable aspiration pump and methods of performing medical procedures to remove clots, thrombus and emboli to re-establish the normal intravascular flow of blood.

18 Claims, 15 Drawing Sheets

ASPIRATION SYSTEMS, DEVICES AND METHODS FOR TREATING ISCHEMIC STROKE

BACKGROUND OF THE INVENTION

For many years catheters have been used to within the vasculature for diagnostics and therapeutic purposes. These therapies include treatments for ischemia in which removal of an occlusion is performed in the vasculature to re-establish normal blood flow. The blockage may be due to thrombus, plaque, foreign objects or a combination thereof. Generally, soft thrombus created elsewhere in the body (for example due to atrial fibrillation) that lodges in the distal cerebrovasculature may be disrupted or dissolved using mechanical devices and or thrombolytic drugs. When treating ischemia in cerebral vessels, small diameter, flexible microcatheters are typically used because they can navigate the tortuous anatomy to access the site of the occlusion. These small diameter microcatheters typically have outer diameters from 1.0 to 2.0 millimeters, inner diameters of 0.5 to 1.5 mm like those described in U.S. Pat. No. 6,197,014 to Samson et al., entitled, "Kink-resistant braided catheter with distal side holes" and are used to deliver therapeutic materials such as clot dissolving drugs, mechanical thrombus retrieval or disruption devices. While guidewires are typically used to disrupt the thrombus, some sophisticated thrombectomy devices have been proposed. For instance U.S. Pat. No. 4,762,130 to Fogarty et al., entitled, "Catheter with Corkscrew-Like Balloon", U.S. Pat. No. 4,998,919 of Schepp-Pesh et al., entitled, "Thrombectomy Apparatus", U.S. Pat. No. 5,417,703 to Brown et al., entitled "Thrombectomy Devices and Methods of Using Same", and U.S. Pat. No. 6,663,650 to Sepetka et al., entitled, "Systems, Methods and Devices for Removing Obstructions from a Blood Vessel" discloses devices such as catheter based corkscrew balloons, baskets or filter wires and helical coiled retrievers. Commercial and prototype versions of these devices have shown only marginal improvements over guidewires due to an inability to adequately grasp the thrombus or to gain vascular access distal to the thrombus (i.e. distal advancement of the device pushes the thrombus distally).

Aspiration or suction may be applied to the catheter lumen to aid in removing the thrombus from the occlusion site. Due to the size of the catheter inner diameter the thrombus is typically broken into smaller pieces to facilitate removal through aspiration. If the thrombus includes organized tissue it may be unable to be broken into small pieces and the larger pieces may become lodged in the microcatheter inner diameter requiring that the entire microcatheter be removed to remove the blockage. Should this occur, valuable time to treat the patient is wasted and may lead to a poor outcome for the patient. There is a need for thrombectomy system that incorporates an optimized catheter having a large lumen and an aspiration pump to rapidly remove thrombus including organized thrombus without fragmenting the thrombus.

SUMMARY

In accordance with one aspect there is provided a medical device system for restoring patency of a body lumen in a mammal. More particularly, there is provided a thrombectomy system which includes an elongate thrombectomy catheter having a proximal end with a hub assembly and a distal end, with proximal, intermediate and distal sections positioned between the proximal end and distal end and an aspiration pump that can be coupled to the catheter proximal end. The elongate catheter is constructed of different polymers having various durometers and includes reinforcement materials to provide a catheter lumen having a large inner diameter, greater than 0.070 inches, and whose distal section can be subjected to a bend radius of two times the inner diameter without kinking. The elongate catheter is has a distal section that preferably includes a helical wire reinforcement and is of a construction that can be subjected to negative pressures of 29 inHg without causing catastrophic damage that would render the catheter unusable.

In accordance with another aspect of the present invention there is provided a thrombectomy system catheter assembly comprising biocompatible resilient materials. Suitable resilient materials include metal alloys such as nitinol, titanium, stainless steel and cobalt chromium and any alloys thereof. Additional suitable materials include polymers such as polyimides, polyamides, fluoropolymers, polyetheretherketone (PEEK), polyurethanes, EPTFE, polyesters and shape memory polymers. These materials may be formed into desired shapes by a variety of methods which are appropriate to the materials being utilized such as extrusion, laser cutting, injection molding, welding, electrochemical machining, machining, photo-etching and casting. The catheter has a design that allows the transmission of a pressure waveform generated by a connected aspiration pump to move from the proximal end of the catheter to the distal end of the catheter with minimal dampening.

In accordance with yet another aspect there is provided an aspiration pump that is compact and disposable and has an extension tube for connecting to a catheter. Typically, the extension tube includes a connector capable of attaching to a rotating hemostatic valve (RHV) that couples the extension tube to the proximal hub of the catheter. The aspiration pump includes a housing that contains the pump assembly, a removable aspiration container, a power module and a programmable controller module. The aspiration pump include may include other modules and components such as a sensor module (for sensing pressure or fluid flow in the system and or cameras for image capture of aspirated clot), an audio module, a display module, a data storage module and an input output module whereby the programmable controller can wirelessly (or via wire) receive and or send programs or data to or from external devices such as computers, phones and tablets.

More particularly, the pump may interface with a connected portable computer or phone to transmit data via cable or wirelessly using Bluetooth, WiFi or other wireless modalities. The data collected by the pump may be uploaded automatically to data registry for prospective and retrospective clinical studies. The embedded software in the pump may be updated remotely via the internet or augmented in real time with data available through the internet. The embedded software in the pump may also be enhanced using artificial intelligence to improve or refine the clot disruptive algorithms utilized during the pumps use.

In accordance with another aspect of the thrombectomy system, the design and construction of the pump extension tube has a non-collapsing, non-expanding tubing structure, that may be similar to the construction to that of the aspiration catheter, such that it mitigates pressure dampening of the pressure wave form or signal from the proximal end of a connected aspiration catheter to the pressure sensor in the pump line. To minimize dampening of the pressure signal from the catheter to the pump sensor the extension tube overall length and inner diameter are controlled.

In accordance with another aspect there is provided a method for performing a thrombectomy procedure using a thrombectomy system that includes an elongate catheter having proximal and distal ends and an inner diameter greater than 0.070 in diameter, an aspiration pump and a connector coupling the catheter and pump. The method includes the steps of:
- providing an elongate catheter having proximal and distal ends and an inner diameter greater than 0.070 in;
- providing an aspiration pump having an aspiration container;
- positioning the distal end of the catheter within a vessel lumen wherein the inner diameter of the catheter distal end is greater than 50% of the inner diameter of the vessel lumen and adjacent a thrombus;
- coupling the aspiration pump to the catheter using a connector;
- operating the aspiration pump to provide negative pressure to the lumen of the catheter thereby suctioning thrombus through the catheter lumen and into the aspiration container;
- withdrawing the catheter from the vasculature.

DETAILED DESCRIPTION

Figure 1:
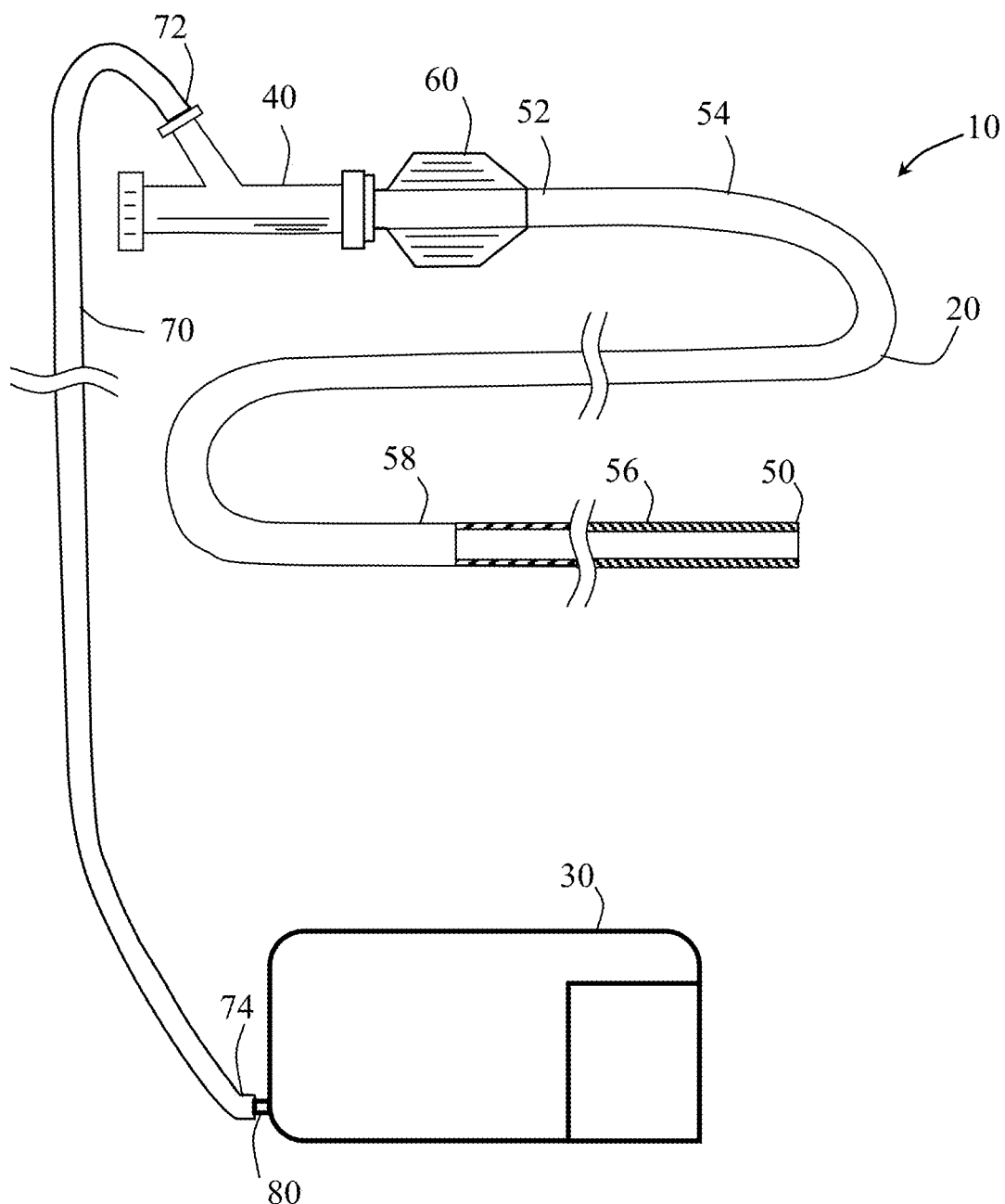
FIG. 1 is a partial cross-sectional view of a thrombectomy system for removing thrombus in a targeted area of the vasculature including a catheter and aspiration pump.

Methods and systems for capturing and removing an embolus or thrombus from an area of the body are herein described. While the terms "thrombectomy" and "thrombus" generally refer to removal of a specific type of embolus, the usage herein should be considered more broadly to include the removal additional types of emboli such as plaque, organized tissue fragments, clots and foreign objects that may block or restrict the normal flow of blood within the vasculature. In other nonvascular lumens within the body, the term "embolus" is herein construed more broadly, to include obstructions of a lumen such as "stones" lodged in a duct. FIG. 1 illustrates an embodiment of a thrombectomy system 10. Thrombectomy system 10 includes an elongate catheter 20, an aspiration pump 30 coupled together using connector 40. Catheter 20 has a distal end 50, a proximal end 52 and proximal, intermediate and distal sections (54, 56 and 58 respectively) positioned between said ends. Located at the proximal end of catheter 20 is a catheter hub 60 that facilitates the connection of connector 40 to the catheter. Connector 40 is also connected to aspiration pump 30 via pump extension tubing 70. Tubing 70 has a first end 72 connected to a port of connector 40 and a second end 74 which is connected to the intake 80 of pump 30.

Figure 2:
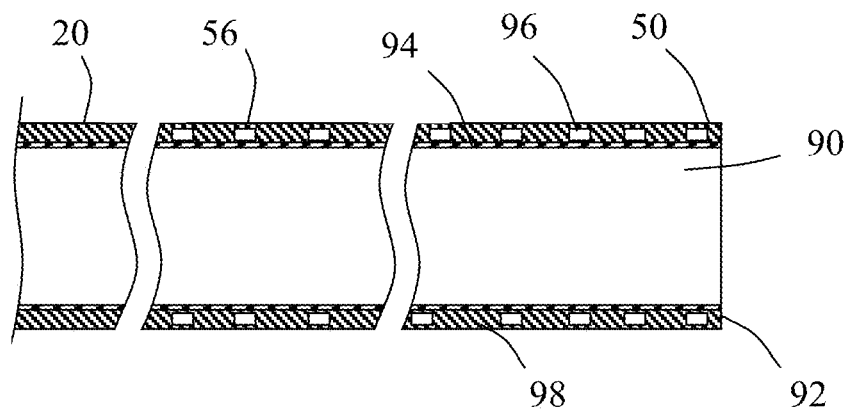
FIG. 2 is an enlarged partial cross-sectional view of the distal end of the catheter.

A partial cross sectional view of distal section 50 of catheter 20 is shown in FIG. 2. As shown, catheter 20 includes a lumen 90 defined by catheter wall 92. The catheter wall 92 at the distal section 50 may include an inner liner 94 surrounded by a helical reinforcement wire 96 and bonded to appropriate polymer 98. While not shown, the construction of catheter 20 may utilize known catheter technologies in the proximal and intermediate catheter sections that incorporate braiding and or coiling using metallic or non-metallic reinforcing filamentous materials to provide high strength while maintaining catheter flexibility. The incorporation of lubricious hydrophilic and or hydrophobic materials on the inner and or outer surface of the catheter is considered to be within the scope of known catheter construction techniques and suitable for use in a thrombectomy system according to embodiments.

With typical microcatheters used in the cerebrovasculature, the distal section of the catheter usually has an outer diameter (OD) of between 1 and 2 millimeters and an inner diameter (ID) of between 0.5 mm 1.5 mm with a wall thickness (WT) of about 0.25 mm which yields inner diameter to total wall thickness ratios of between 1.0 to 3.0. In this ratio range catheters generally have sufficient integrity to be navigated to a target site to perform their intended function. As this ratio decreases below 1.0 the catheters generally become too stiff and or the lumen size is too diminished to function for aspiration of thrombus. Similarly for ratio increases above 3.0 the catheters may become too flimsy to access a desired location or collapse under negative pressure (unless designed with sufficient high strength reinforcement). In a preferred embodiment the optimized catheter 20 has a wall thickness of about 0.25 mm and inner diameter greater than 2.0 mm yielding an ID to total wall thickness ratio greater than 4.0 while incorporating a helical reinforcement wire 96 as shown in FIG. 2. The helical reinforcement wire may be formed suitable biocompatible resilient materials including nitinol, stainless steel, titanium, cobalt chromium, carbon fiber, glass fiber and polymeric fibers like nylon, Kevlar or Spectra.

Figure 3:
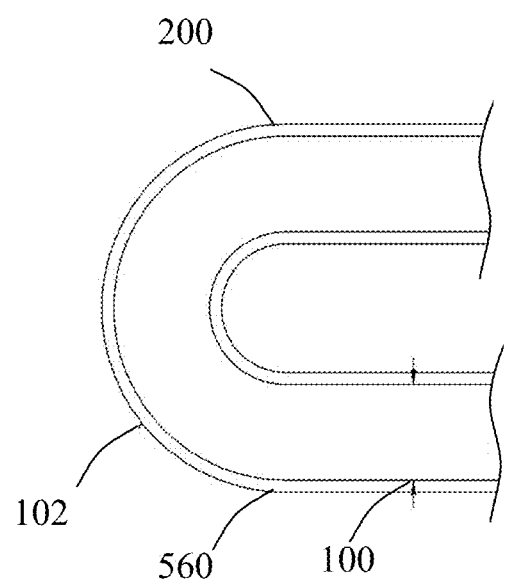
FIG. 3 is an enlarged partial cross-sectional view of the distal end of the catheter placed in a bent configuration.

FIG. 3 shows a partial cross sectional view of distal section 56 of catheter 20 positioned in a bend. As previously discussed the preferred embodiment incorporates a helical reinforcement wire 96 which surrounds the inner diameter 100. With optimized construction the distal section 56 of catheter 20 can be positioned in a bend such that the outer diameter bend radius 102 is two times the inner diameter without kinking when the inner diameter is greater than 0.070 in.

Figure 4A:
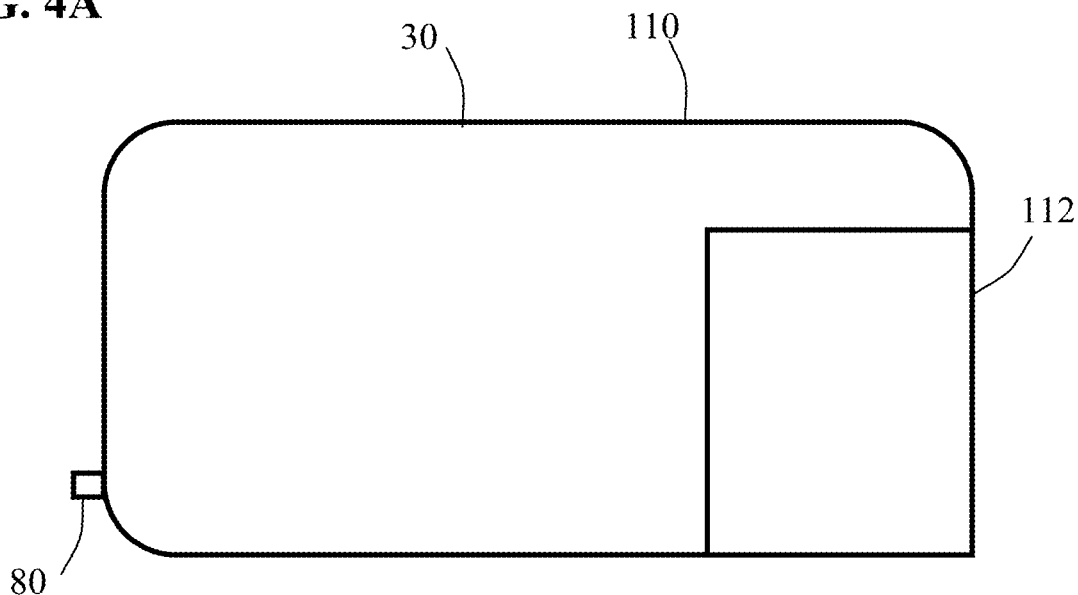
FIG. 4A-4C are respectively a side view of the aspiration pump, a schematic of the pump functional modules and a top view of the aspiration pump of the thrombectomy system of FIG. 1.
Figure 4B:
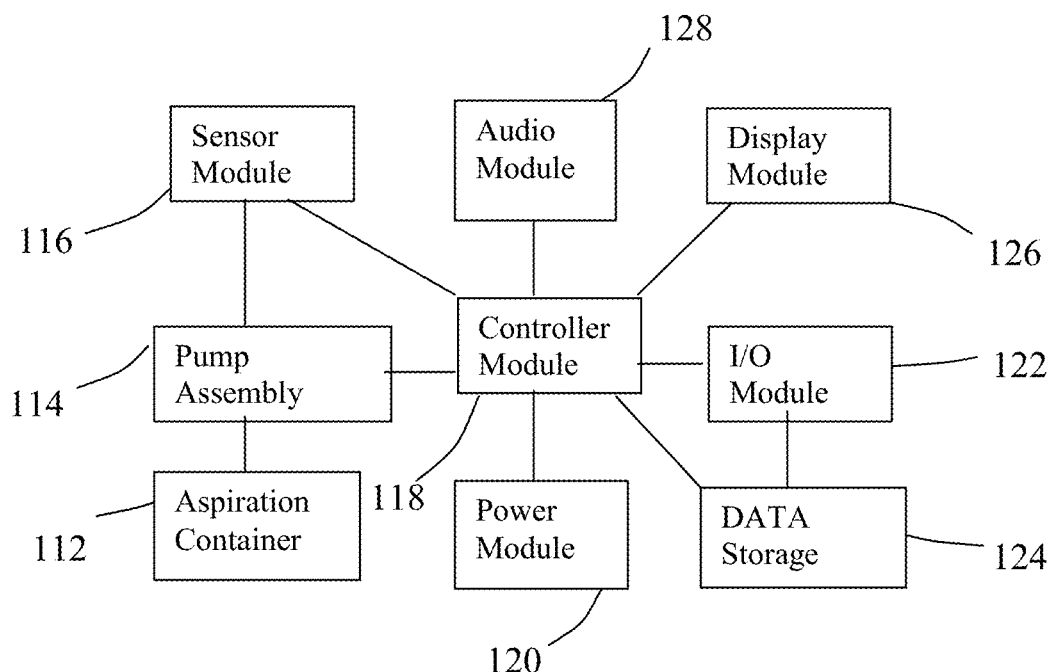
Figure 4C:
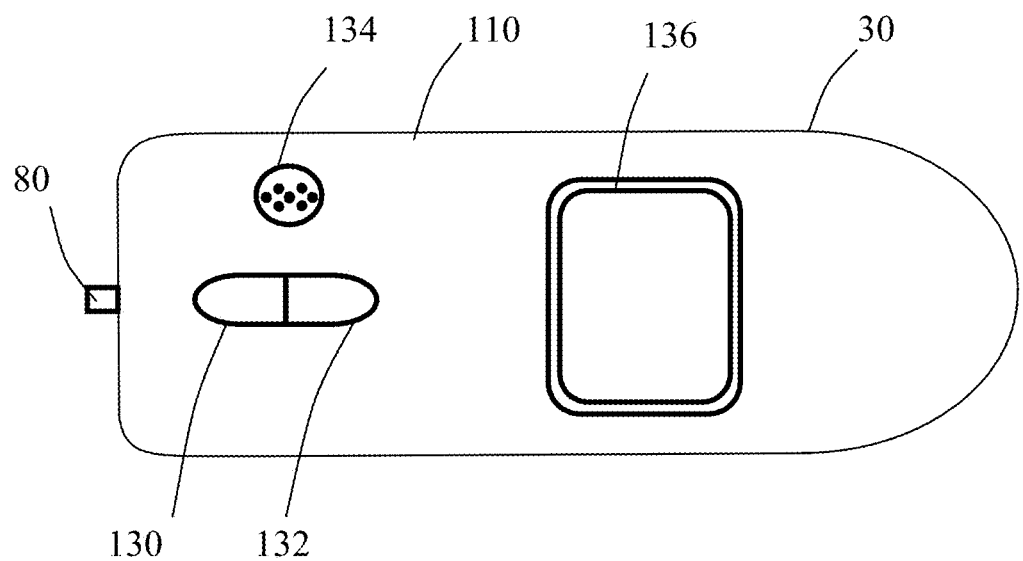

In addition to catheter 20, the thrombectomy system 10 includes aspiration pump 30 is shown in FIG. 4A. Aspiration pump 30 includes a housing 110 and a removable aspiration container 112. FIG. 4B illustrates the functional components of the pump contained within housing 110. The components include a pump assembly 114, a sensor module 116, a programmable controller module 118 and a power module 120. The aspiration pump includes other modules such as an input/output module 122 whereby the programmable controller module can wirelessly receive or send programs or data to or from external devices, a data storage module 124, a display module 126 and an audio module 128. The controller module may take the form of an integrated controller module that includes a microprocessor, data storage, input/output hardware or other additional modules and capabilities. The controller module 118 is capable of controlling the pump assembly 114 to provide negative pressure to the catheter and thus suction when removing thrombus. The controller also has the capability to alternate between negative and positive pressure to apply a dynamic load to thrombus to dislodge any thrombus that may become lodged in the distal end of the catheter. The pump has a limiting feature that does not apply positive pressure in such a way that thrombus or debris is expelled from the distal end of the catheter. The frequency of alternating between negative and positive pressures as well as the magnitude of the pressure can be wirelessly input to controller via the input/output module using known wireless protocols including Bluetooth and WIFI. Alternatively, the controller may be programmed manually using the lighted first and second push buttons 130 and 132 respectively, positioned on the top of housing 110 shown in FIG. 4C. Also located on housing 110, are speaker 134 and display 136. Speaker 134 is used to provide audible feedback to the user during programming of the controller and operation of the thrombectomy system. Display 136 provides visual feedback for the pressure settings as well as data from the sensor module monitoring the pressure. Display 136 is coupled to the programmable controller module and is preferably a Thin Film Transistor liquid crystal display with touch screen capability however other types of display screens may be suitable. Together the first and second push buttons 130 & 132, speaker 134 and display 136 form a user interface that allows for programming of the controller, display of data during pump operation and providing feedback for any alarms. For instance, an alarm may be set to trigger when negative pressure reaches a certain limit. When the alarm is triggered the user interface may provide feedback to the user in the form of alternating flashing of first and second push buttons, audible chirping through the speaker, flashing of the display or any combination thereof, informing the user to take some action.

The pump can provide positive and negative pressure conditions and waveforms to any fluids in the line by connecting the distal end of the pump extension tubing (preferably having a Luer connector) to the hub of the aspiration catheter. The pump can measure the pressure of the fluid in the line immediately distal to the pump outlet but proximal to the pump extension tubing. The pump extension tubing is preferably about 16 inches long, and constructed of flexible tubing (preferably non-expanding) having an Inner Diameter approximately equal to or slightly greater than the ID of the associated aspiration catheter. The pump extension tubing is used to connect the hub of the aspiration catheter to the inlet of the disposable pump housing. The pump positive and negative pressure conditions and waveforms are automatically managed via the software embedded on the onboard microprocessor, motor driver electronics, stepper motor, and peristaltic pump hardware. The real-time pressure readings of the fluid in the line just distal to the pump outlet are continuously monitored by the microprocessor when the pump is in the "on" position or operating.

The sharpness of the cyclic waveform delivered to the end of the aspiration catheter can be significantly improved by programming the embedded software to not just stop the pump during the vacuum portion of the cycle, but run the pump in a positive pressure mode for a portion of the non-vacuum cycle to decelerate the vacuum signal faster than can be naturally dissipated. Additionally, running the positive pressure mode slightly longer than the pressure sensor reads at the pump to achieve a near zero-gauge pressure at the tip of the aspiration catheter (mitigating the limitations of blood pressure) so that when the vacuum mode of the cycle restarts it will provide the maximum acceleration of vacuum pressure possible to the end of the aspiration catheter once again. Maximum disruptive forces are delivered to the blood clots at the end of the aspiration catheter during maximum acceleration and deceleration pressure inflection points in the waveform of the pump pressure signal. Thus, the "squarer" the waveform, the more disruptive the pump will be to the clot in the inner lumen of the catheter and thus the easier it will be to aspirate the clot through the pump extension tubing. To provide this high frequency square wave, all components of the pump from the processing speed of the onboard microprocessor, pressure sensor, motor driver electronics, stepper motor, and peristaltic pump hardware have been designed to handle these input forces with tight tolerances to mitigate slop in the intended fluid movement during the cycle.

In one embodiment of system operation, when the pump is prepped, connected to the aspiration catheter, and initially placed in the "on" position, and if the in-line pressure sensor indicates that fluid in the line is "free flowing", the pump will provide a steady full vacuum pressure ramp up until the pressure sensor indicates fluid in the line is "restricted". Otherwise, the pump will shut off after 30 seconds to mitigate blood loss.

Once the pump pressure sensor indicates that the fluid in the line is "restricted", the embedded software will instruct the pump to run thru a series of cyclic pressure varying waveforms starting with a minimal amplitude change and low frequency (using only vacuum) to a maximum amplitude change and high frequency (using vacuum and positive pressure). During each variation, the embedded software will utilize sensors to sense, simultaneously, fluid in the line and the state of the fluid movement. If the sensor detects the fluid in the line is "moving", the pump will maintain the current cyclic pressure waveform until the sensor detects the fluid in the line is in a "free flowing" state and then it will run for 30 more seconds and shut off.

For the most demanding clots, versions of the pressure waveform will be generated where the positive pressure will exceed the blood pressure. This increase in pressure above blood pressure will force the clot to move slightly away from the tip of the aspiration catheter and then return the clot back on to the tip of the aspiration catheter on the next vacuum cycle. The continuous impact of clot at ever increasing frequencies and amplitudes will increase the disruptive energy delivered to the clot and thus increasing the chances of aspirating the clot thru the aspiration catheter. The disruptive energy is increased in the modification because the use of momentum related to the full mass of the clot is employed, not just the mass of the clot in the catheter. Additionally, the deceleration of the clot impacting the tip of the catheter is more pronounced.

During a thrombectomy procedure, the pump will record pressures, fluid flow states and or rates, images and time data onto its onboard memory. Prior to shutting off, the pump will transmit the information via wired or wirelessly connected devices and or enabled applications for record keeping and or graphical display. Additionally, the onboard camera will log, store (and transmit when requested) an image or video (collection of images at a predetermined frame rate) of the clot collected on a preferably gridded clot capture screen located inside the removable clot aspiration container positioned within the pump. The following is a subset of the expected information collected:

Pump Total Operation Time,

Pump Waveform and time required to reach successful movement and free flow,

Clot image.

Using the data collected above, connected enabled devices can cross reference the collected data with previously validated data sets of pre-clinical and clinical data to analyze the clot and provide a likely determination of clot volume, clot morphology and clot age.

Figure 5:
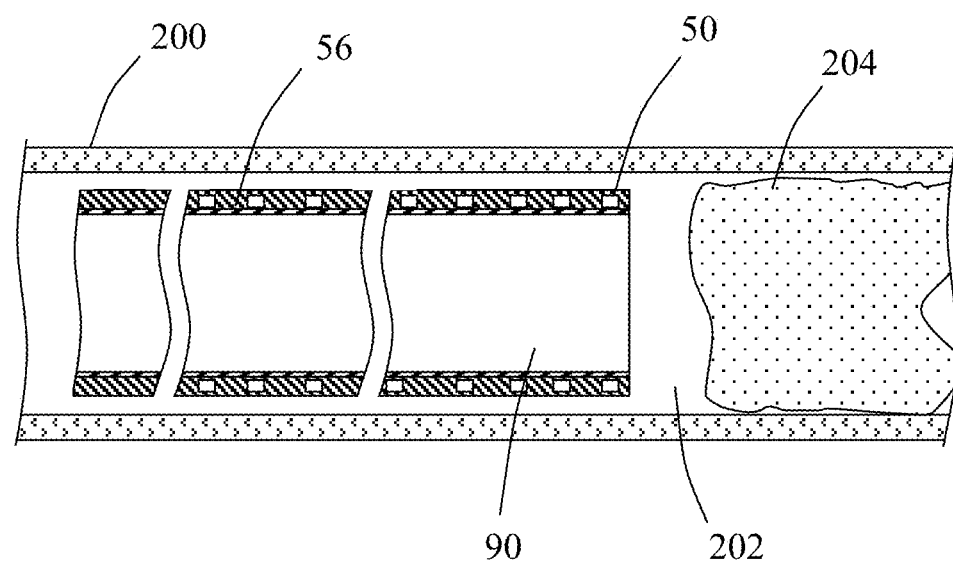
FIG. 5 is a partial cross sectional view of the distal end of the catheter, shown in FIG. 1, positioned within the lumen of a vessel adjacent a thrombus.

As previously discussed, small diameter microcatheters that have been used in the past to for thrombus removal have difficulty in removing thrombus partially due to the small catheter lumen requiring the piecemeal breakup of the thrombus into smaller pieces. Additionally these small diameter microcatheters have difficulties in removing thrombus through aspiration because the diameter of the catheter lumen in relation to the inner diameter of the vessel in which the thrombus is lodged is generally in the range of 30 to 40 percent. During aspiration, this difference in diameter allows blood positioned proximal to the distal end of the catheter to be drawn into the catheter reducing the amount of suction being applied directly to the thrombus. To compensate for the reduced suction force the catheter tip is typically positioned directly adjacent or in contact with the thrombus which can cause the catheter lumen to become plugged. FIG. 5 illustrates catheter 20 of thrombectomy system 10 located within a vessel 200. The distal section 56 of catheter 20 is situated within vessel lumen 202 whereas the catheter distal end 50 is positioned adjacent the thrombus 204. As shown in FIG. 5 the diameter of catheter lumen 90 is greater than 50 percent of the diameter of vessel lumen 202. When the catheter lumen to vessel lumen ratio is greater than 50 percent aspiration through the catheter lumen becomes more efficient the suction force from aspiration is directed more towards the thrombus as opposed to suctioning blood positioned proximal to the catheter distal end. This increased suction efficiency allows the thrombus to stretched and drawn into the catheter lumen typically without fragmentation.

Figure 6:
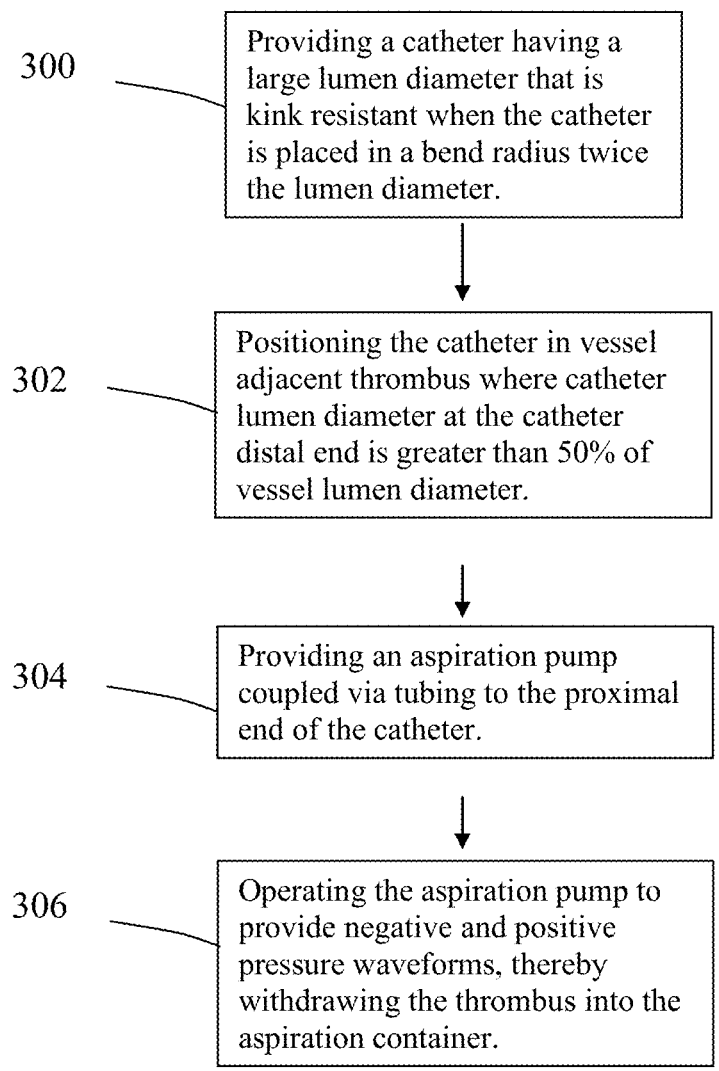
FIG. 6 is a method of removing a thrombus from a vessel using a thrombectomy system shown in FIG. 1.

FIG. 6 shows a method of performing a thrombectomy procedure using thrombectomy system 10. The method comprises the steps of:

providing an elongate catheter having proximal and distal ends and an inner diameter greater than 0.070 in;

positioning the distal end of the catheter within a vessel lumen wherein the inner diameter of the catheter distal end is greater than 50% of the inner diameter of the vessel lumen and adjacent a thrombus;

providing an aspiration pump having an aspiration container;

coupling the aspiration pump to the catheter using a connector;

operating the aspiration pump to provide negative and positive pressure to the lumen of the catheter thereby suctioning thrombus through the catheter lumen and into the aspiration container;

withdrawing the catheter from the vasculature.

When operating thrombectomy system 10 according to the aforementioned method steps, thrombus can be efficiently and effectively removed from the vasculature.

Figure 7:
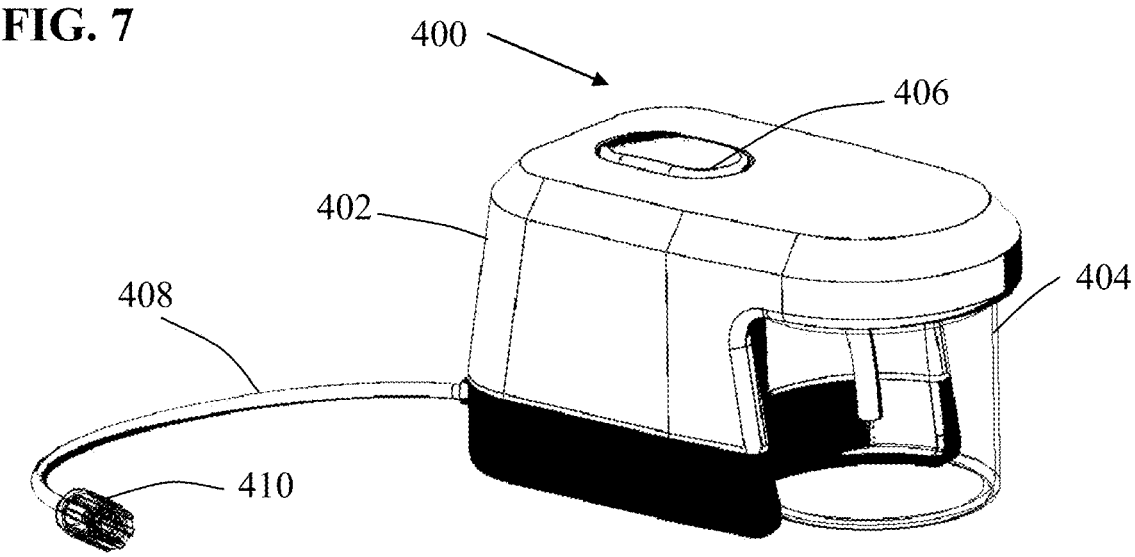
FIG. 7 is a perspective view of another embodiment of an aspiration pump for use in thrombectomy procedures.

FIG. 7 illustrates another embodiment of an aspiration pump 400 for use in thrombectomy procedures. The aspiration pump includes a housing assembly 402, a removable aspiration container 404 having a lid 405 (not shown) for aspirated clot collection, a push button 406, and pump extension connector tubing 408 that includes a connector 410 adapted to connect to a catheter.

Figure 8:
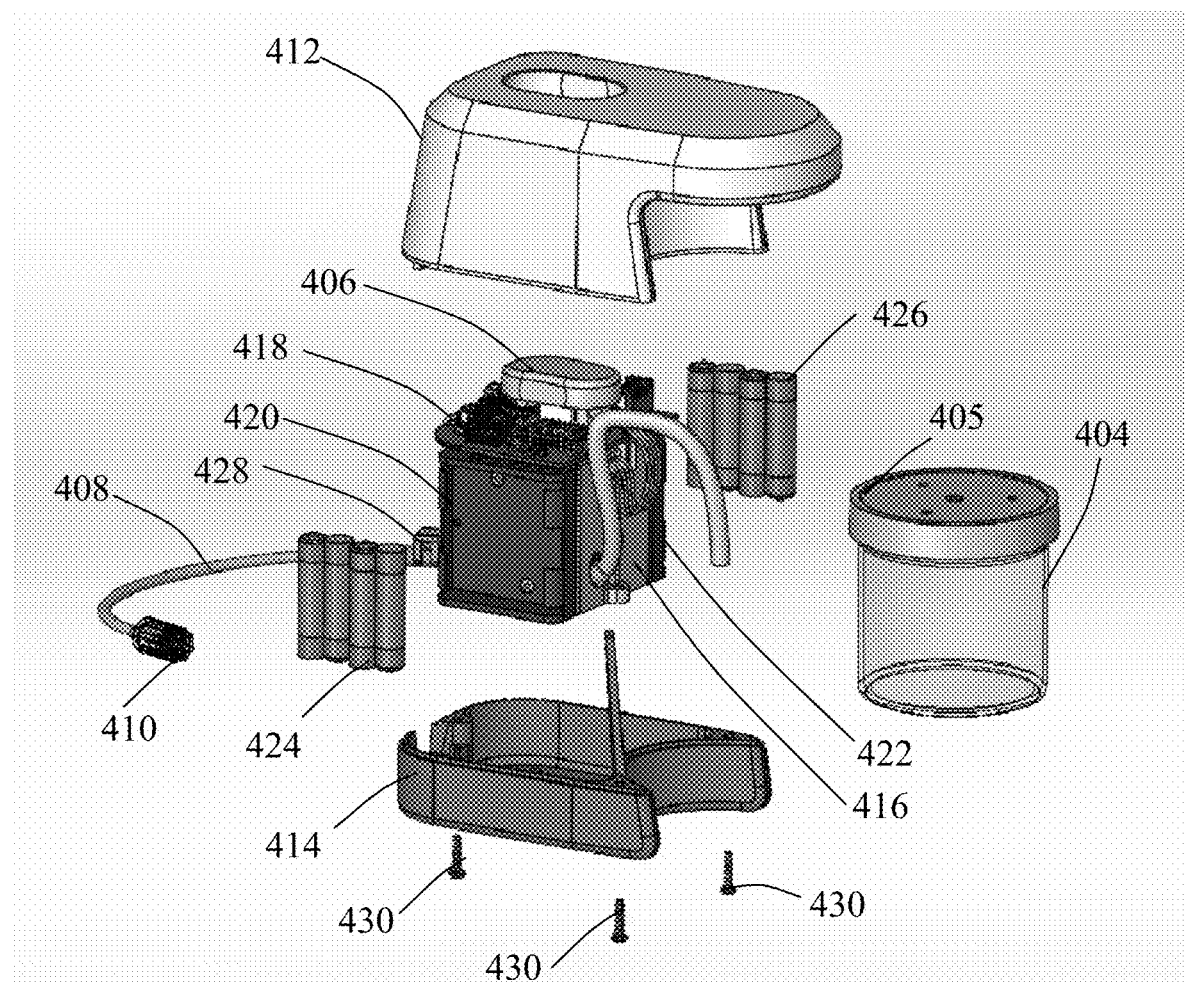
FIG. 8 is an exploded perspective view of the aspiration pump shown in FIG. 7 illustrating internal components.

FIG. 8 illustrates the functional components of the aspiration pump 400 contained within the upper and lower housing portions 412 and 414 respectively, in an exploded view. The main components include a pump assembly 416, a controller board 418, and a power supply in the form of battery clips 420, 422 that hold battery packs 424, 426. As can be appreciated the power supply could be of a conventional ac design and be configured to plug into a wall outlet using an electrical cord. The controller board 418 includes previously discussed control modules and can be considered as an embodiment of an integrated controller module containing a microprocessor, input output data hardware, data storage and other modules as desired. Removable aspiration container 404 is shown preferably formed from a transparent plastic material. Suitable transparent materials include glass or plastics such as polystyrene, polycarbonate, polymethylmethacrylate, acrylics and clear polyolefins. Removable lid 405 having several apertures is shown on aspiration container 404. The controller board 418 includes a programmable controller module in addition to user interface components such as the push button 406 (which may include static or blinking lights or LED's in multiple colors and an audio module), sensor connectors for pressure sensor 428, on board data storage as well data input/output modules whereby the programmable controller can receive or send programs or data to or from external devices. The data input/output modules are capable of sending or receiving data via wired or wirelessly connected devices using Bluetooth, Wi-Fi or other wireless protocols and hardware. The upper and lower housing portions 412, 414 are held together when assembled using fasteners 430.

Figure 9:
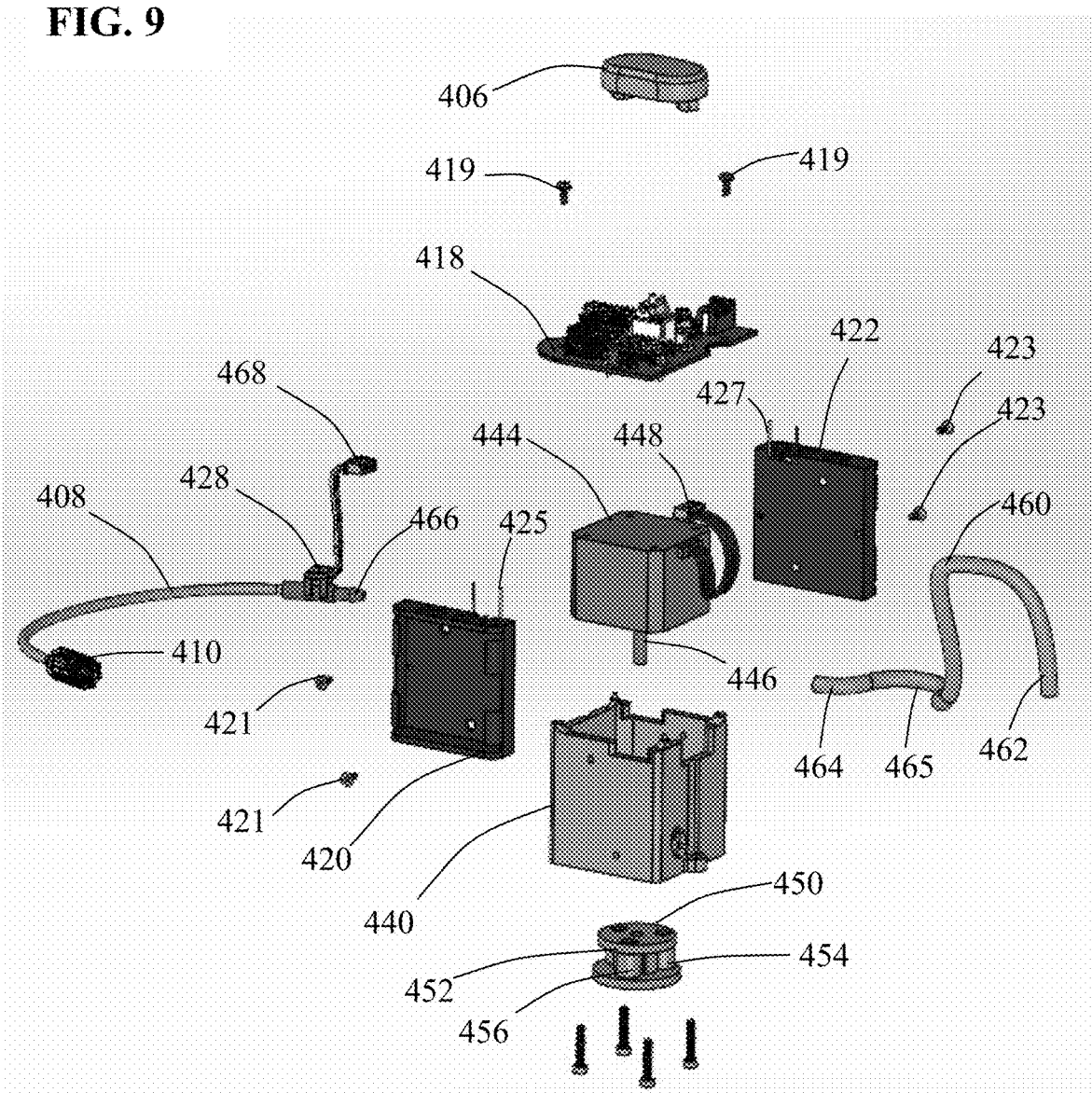
FIG. 9 is an exploded perspective view of the pump assembly shown in FIG. 8 illustrating internal and adjacent components.

FIG. 9 shows an exploded view of the pump assembly 422 and components connected to it. The components include the controller board 418, a pump assembly housing 440, battery clips 420,422, the connector tubing 408 (with sensor 428). The controller board 418 is attached to the top of the pump assembly housing 440 using fasteners 419 whereas the battery clips 420,422 are mounted on front and back sides of the housing using fasteners 421, 423. Also illustrated are components located within the pump assembly housing 440 which include a motor 444 (preferably a stepper motor however other motor types with an encoder for controlling rotation, speed and position are also suitable) having a shaft 446 and a motor connector 448 that connects the motor to controller board 418. Shaft 446 is coupled to a circular rotor 450 having multiple rollers 452, 454, 456. When assembled rotor 450 is positioned adjacent pump aspiration tubing 460 which has a first end 462, a second end 464 and a rotor portion 465 within pump assembly housing 440. First end 462 of the aspiration tubing extends through the side of the pump assembly housing 440 and configured to be positioned in the aspiration container (not shown). Second end 464 of the aspiration tubing 460 extends through the opposite side of pump assembly housing 440 and connects to the connector tubing 408 at connector tubing end 466 adjacent sensor 428. A rotor portion 465 of the aspiration tubing 460 is placed in a curved position within the pump assembly housing 440 between the pump assembly housing wall and the rollers of the rotor 450. The motor, sensor and battery clips all include electrical connectors such as motor connector 448, sensor connector 468 and battery clip connectors 425, 427 that couple to the controller board 418 and controller module.

Figure 10A:
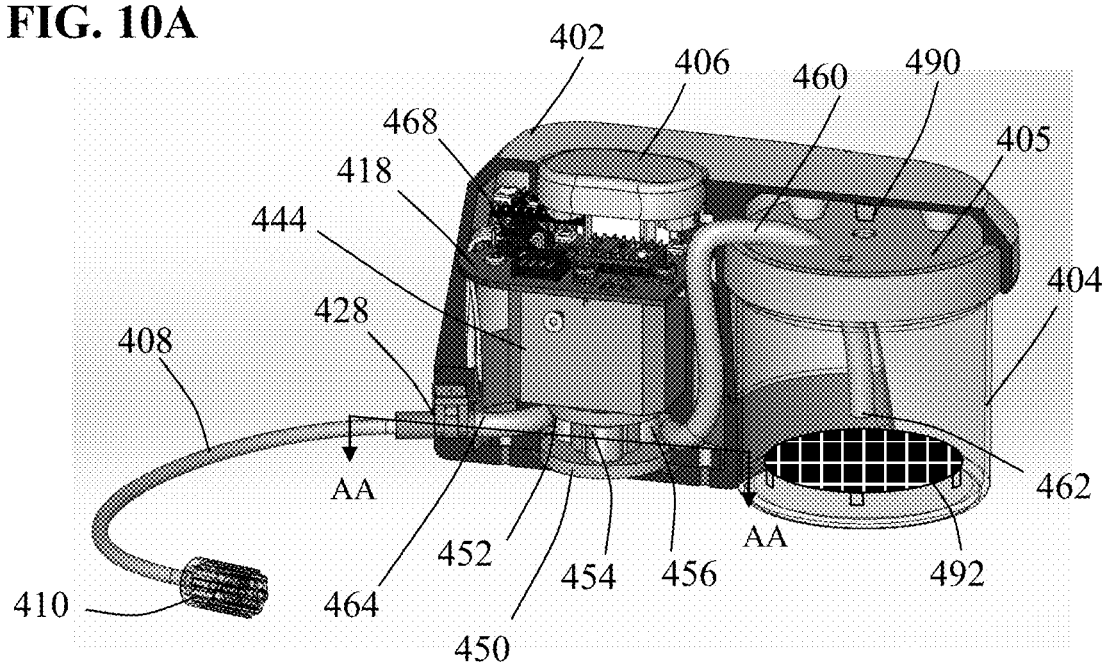
FIG. 10A is a front partial sectional view of the aspiration pump of FIG. 7.
Figure 10B:
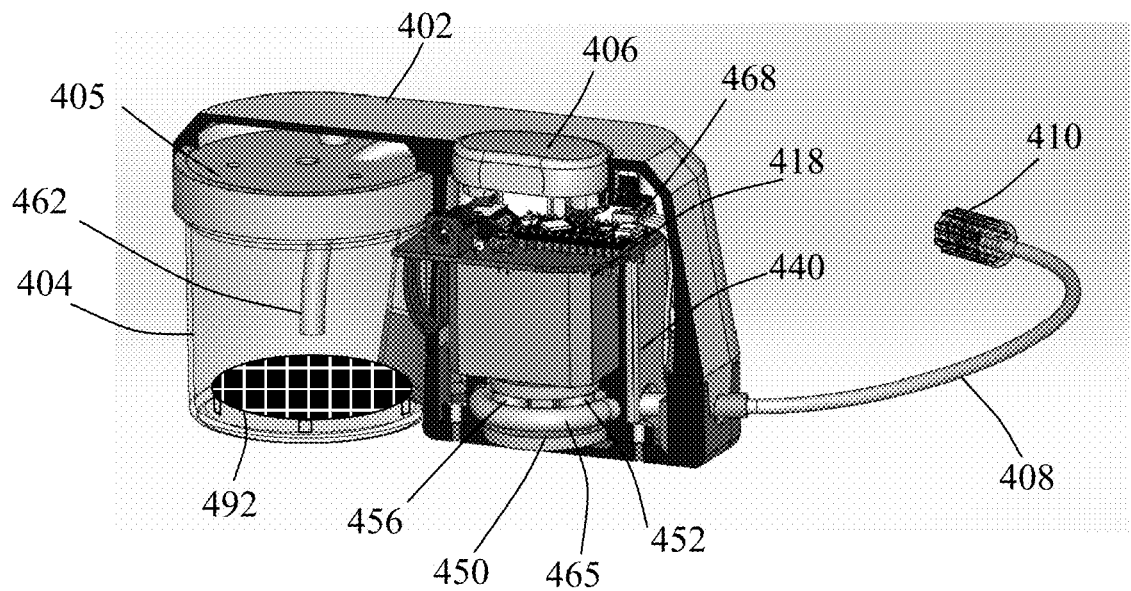
FIG. 10B is a rear partial sectional view of the aspiration pump of FIG. 7.

FIGS. 10A and 10B show front and rear perspective views of the assembled aspiration pump with the housing assembly 402 being partially sectioned. To illustrate the position of the first and second ends 462, 464 of the aspiration tubing 460 along with the aspiration tubing rotor portion 465 that contacts the rollers of the rotor 450, the battery clips are removed, as is the lower portion of the pump assembly housing 440. As previously discussed, a second end 464 of the aspiration tubing 460 is connected to the connector tubing 418 at the connector tubing end 466 with rotor portion 465 of the aspiration tubing placed in a curved configuration and then extending through the opposite pump assembly housing wall where a portion of the tubing extends vertically so that first end 462 may enter the lid 405 of the aspiration container 404. Camera 490 is positioned within housing assembly 402 adjacent aspiration container 404 so that an image or video of aspirated clot may be captured on the clot collection filter screen 492 which is preferably gridded to aid in image analysis. The sensor 428 located on the connector tubing 418 is preferably an in-line pressure transducer that is capable of providing pressure readings to the controller board 418 (and controller module) as well as determining whether or not there is fluid flow through the connector tubing 418. Alternative sensors and configurations that include fluid flow sensors and or multiple pressure sensors (not shown) can be utilized on connector tubing 408 to provide feedback information verifying accurate readings and or providing a safety back up are also suitable.

Figure 11:
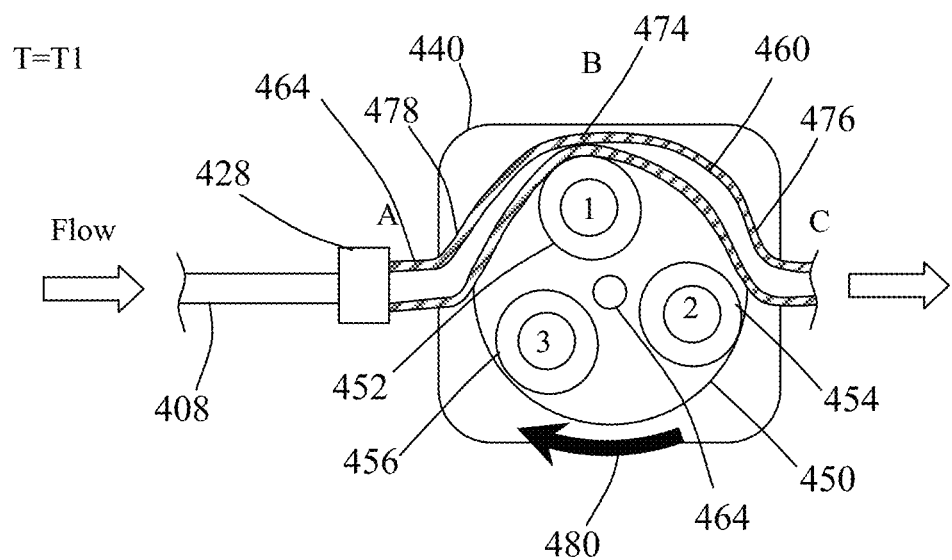
FIG. 11 is a partial sectional view of the aspiration tubing positioned about the rotor at first and second time points during pump operation.
Figure 11:
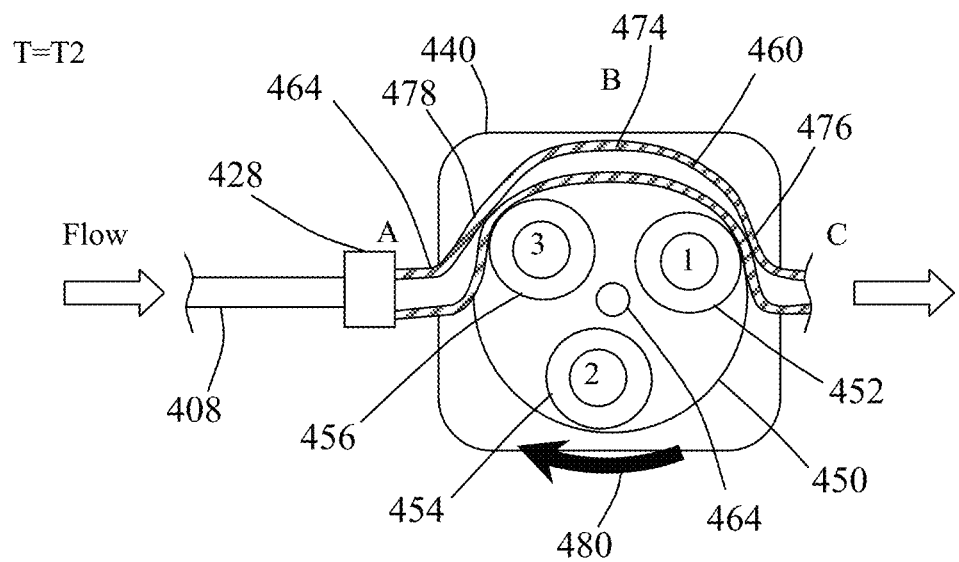

FIG. 11 shows a sectioned view of the lower portion of the pump assembly housing 440 (shown in FIG. 10A) when the aspiration pump is operating at first and second time points, T1 and T2 respectively. As previously discussed, the aspiration tubing 460 extends through a first wall of the pump assembly housing with rotor portion 465 curved around the rollers of the rotor 450 and extends through a second opposite wall of the pump assembly housing. The sensor 428 of the connector tubing 408 and second end 464 of the aspiration tubing 460 is located near position A, while the aspiration tubing exits the pump assembly housing 440 near position C. During aspiration pump operation, the controller supplies power to the motor which causes the motor shaft and connected rotor to rotate in a first rotational direction 480 (clockwise). At time point T1, Roller 452 is shown at a position 474 (position B) compressing the resilient flexible walls of the aspiration tubing such that the lumen of the aspiration tubing is in a sealed configuration. The aspiration tubing fore and aft (positions 476, 478) adjacent Roller 452 is unsealed open. At this point, Roller 456 is at a position that is not compressing the aspiration tubing in a sealed configuration. At time point T2, the rotor 450 has been rotated in the first direction 480 such that Roller 452 is shown at position C and Roller 456 is shown at position A where both rollers are compressing the aspiration tubing in a sealed configuration at positions 476,478 but the walls of the aspiration tubing 460 positioned between the contact points of the rollers 452, 456 are resiliently uncompressed and the tubing lumen is open. The rotation of the rollers in the first rotation direction 480 creates a peristaltic motion with fluid in the aspiration tubing causing a vacuum (applying negative pressure) which draws fluid flow from the connector tubing 408 through the aspiration tubing 460 from position A to position B to position C. The operation of the pump in this fashion corresponds to previously provided descriptions of running the pump in a negative pressure or vacuum mode and providing negative cyclic pressure waveforms.

Figure 12:
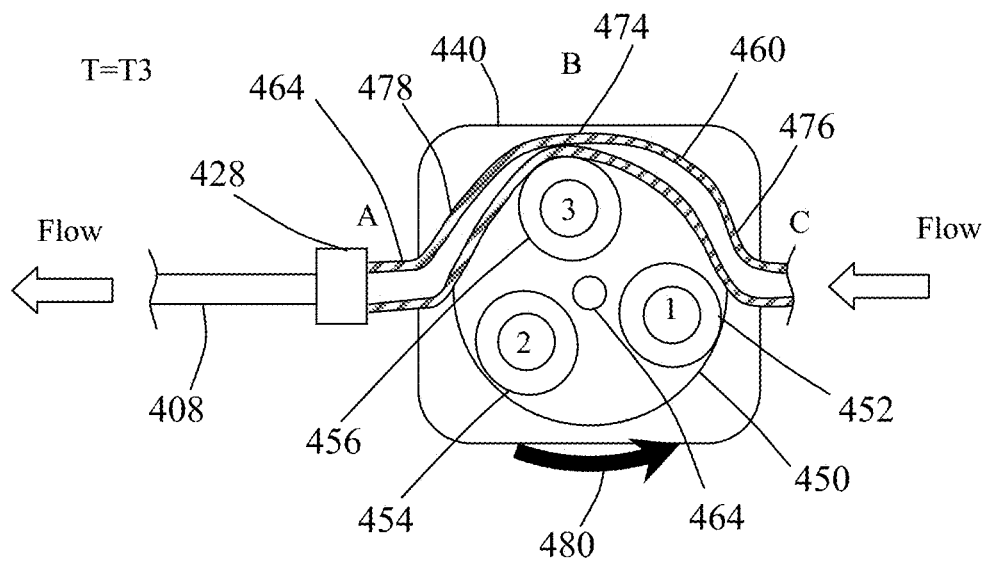
FIG. 12 is a partial sectional view of the aspiration tubing positioned about the rotor at third and fourth time points during pump operation.
Figure 12:
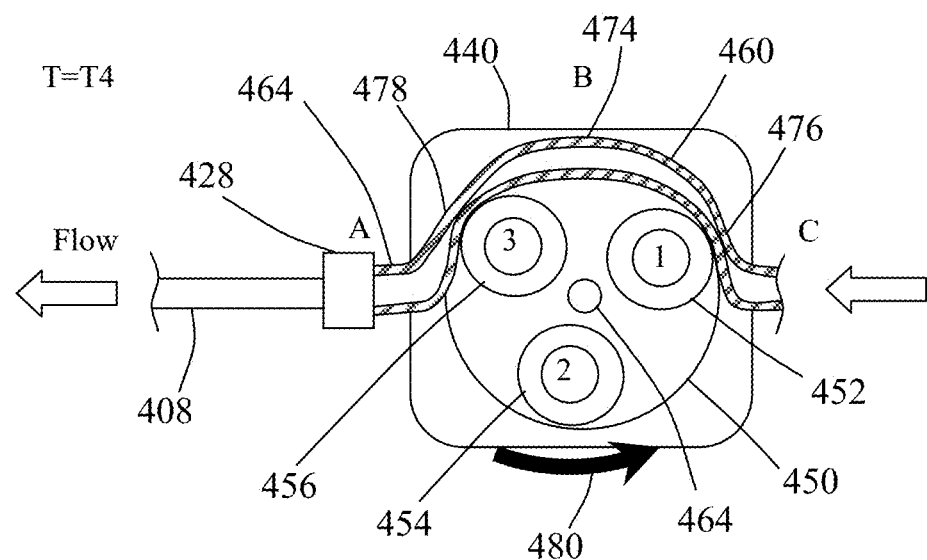

FIG. 12 shows the same sectioned view of the lower portion of the pump assembly housing (shown in FIG. 10A) when the aspiration pump is operating at third and fourth time points, T3 and T4 respectively when the rotor rotation direction 480 is opposite (counterclockwise) to what was depicted in FIG. 11. At time point T3, Roller 456 is shown at a position 474 (position B) compressing the resilient flexible walls of the aspiration tubing portion such that the lumen of the aspiration tubing at position 474 is in a sealed configuration. The aspiration tubing at fore and aft positions 478, 476 adjacent Roller 456 are shown uncompressed with an open lumen. At this point, Roller 452 is at a position that is not compressing the aspiration tubing in a sealed configuration. At time point T4, the rotor has been rotated in the second (counterclockwise) direction such that Roller 452 is shown at position C and Roller 456 is shown at position A where both rollers are compressing the aspiration tubing in a sealed configuration positions 478, 476 but the walls of the tubing between the contact points of the rollers 456,452 position 474 are resiliently uncompressed and open. The rotation of the rollers in the second rotation direction creates a peristaltic motion with fluid in the aspiration tubing applying a positive pressure to the connector tubing 408 which supplies fluid flow through the aspiration tubing 460 from position C to position B to position A. The operation of the pump in this fashion corresponds to previous descriptions of running the pump in a positive pressure mode or providing positive cyclic pressure waveforms.

The operation of the pump utilizing the configurations shown in FIGS. 11 & 12 are controlled by the controller board which sends signals to the motor 444 to operate speed, position and direction. With this level of control the pump can immediately switch from providing a negative pressure cyclic waveform with the motor operating in a first rotational direction (in conjunction with the connected rotor) to providing a positive pressure cyclic waveform with the motor operating in a second opposite rotational direction (in conjunction with the connected rotor). By utilizing aspiration tubing having a known diameter, wall compliance, lumen diameter in conjunction with specifications for the rotor diameter and position of the rollers, the motor can be accurately controlled to deliver or aspirate a specific volume of fluid in a desired time frame as specified by the controller board, or more particularly algorithms or programs previously stored or otherwise provided to the controller board. When paired with an appropriate catheter (or properly calibrated) the pump can alternate between supplying negative pressure and a fast positive pressure waveform to the catheter should the catheter lumen be restricted with clot where the fast positive pressure waveform may have a high amplitude but the volume delivered is very low, so that the clot may be dislodged from within the catheter lumen but not expelled from the catheter tip. This functional operation of the pump allows The use of inline sensors coupled to the pump (whether pressure, flow rate or other) can be utilized by the controller board to aid in verification that a particular algorithm or program is being effective at producing a desired pressure waveform or based on the signals provided cause the controller board to make alterations to the motors operation (and hence pump operation) or switch to alternative programs or operable modes for controlling the pump to achieve the desired outcome.

When coupled to an appropriate catheter the aforementioned aspiration pump 400 is well suited to perform aspiration of clots during a thrombectomy procedure. In an example the aspiration pump may be operated in conjunction with a suitable catheter in in the following manner:

Power up the aspiration pump

A Blinking green light may indicate to the user the model or version of the pump such as a dynamic version of the aspiration pump that is in "standby" mode. In this mode the pump is powered and awaiting initiation from the user. It would be appropriate to be in this "standby" mode while tracking the catheter is being positioned in the vasculature.

A few cm's prior to engaging clot with the tip of the catheter, toggling the button "ON" (either direction) activates the pump and changes the indicator light to "solid blue" indicating that the pump is running in "Constant Aspiration" mode but has not achieved MAX vacuum. This mode is recommended prior to engaging clot.

Should the distal tip of the catheter engage clot and flow through the catheter is restricted, the indicator light alternates "white and blue" indicating a change in the pump operation to a "Dynamic Aspiration" mode. This mode is designed to facilitate the "True Clot" capture and engulfing the clot into the aspiration catheter lumen.

If the "Dynamic Aspiration" mode resolves the restriction and the clot is fully captured into the pump reservoir and the indicator the light turns back to "solid blue" indicating a change in the pump operation to "Constant Aspiration" mode. The procedure is complete and the user can toggle the switch to the middle position returning the pump to "stand by" mode If the "Dynamic Aspiration" mode is unable to resolve the restriction in a predetermined number of cycles (between 2-5 mins depending on the clinical situation), the indicator light will turn "Solid Red" indicating that pump has returned to "Constant Aspiration" mode and has achieved MAX vacuum pressure. This is the appropriate situation for traditional retraction of the aspiration catheter and clot proximally. If during retraction of the aspiration catheter, the clot disengages or restriction is lost, the indicator light will turn "solid blue" again indicating "Constant Aspiration" mode again but not holding MAX Vacuum. The user can then re-engage the clot by moving the aspiration catheter distally and starting the cycle over from the beginning.

The "Constant Aspiration" and "Dynamic Aspiration" illustrate two pump operation modes that may be used to facilitate clot capture. In the "Constant Aspiration" mode the pump operates to achieve a maximum vacuum state. This mode is akin to applying a vacuum to the catheter using any available vacuum source (e.g. simple vacuum pump, room or suite available vacuum). In the "Dynamic Aspiration" mode the aspiration pump delivers a predetermined cyclic waveform to the catheter to facilitate clot capture. The cyclic wave form may include alternating magnitudes and durations of negative and positive pressure in order to stretch and pull the clot into the catheter. While it is possible to form a cyclic wave form using a room vacuum source or simple vacuum pump in combination with a controllable vent valve this only allows pressures up to atmospheric pressure and would be difficult to control or obtain sharp wave form transitions.

Figure 13:
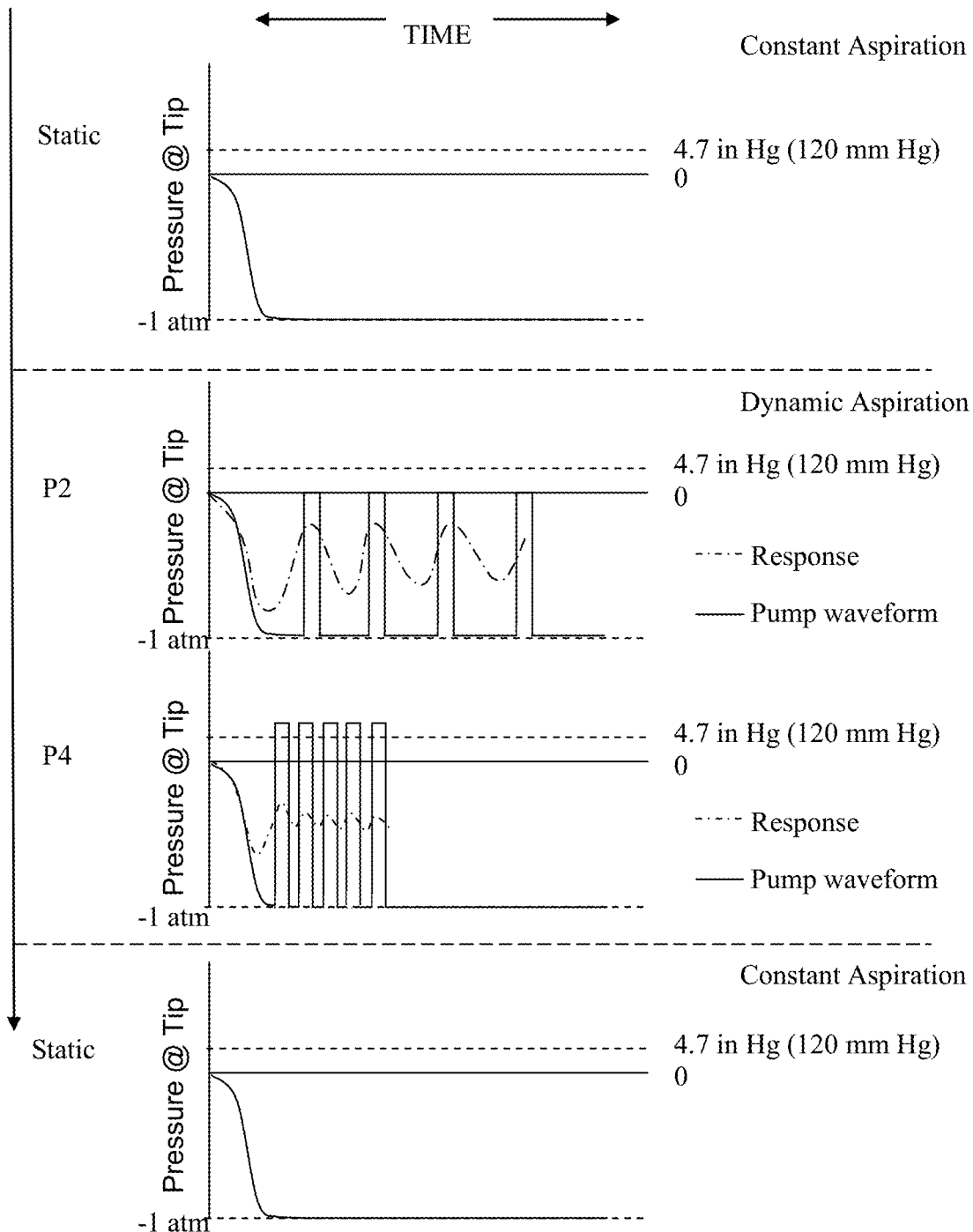
FIG. 13 is a schematic diagram of exemplary applied pump waveforms usable during a thrombectomy procedure.

In the previously presented example, a condition was presented in which the "Dynamic Aspiration" mode was unable to resolve the restriction and then switched to "Constant Aspiration" mode. With the appropriate waveforms loaded into the programmable controller, instead of switching to the "Constant Aspiration" mode the pump can remain in the "Dynamic Aspiration" mode and sequence through additional waveforms such as those shown in FIG. 13 (P2 & P4) prior to switching to "Constant Aspiration" mode. These additional waveforms may be more suited to different clot types including those with varying degrees fibrin, organization or calcification and therefore be more apt to capturing the clot. Due to the peristaltic nature of the aspiration pump 400, the ability to accurately control the motion of the motor 444 and feedback from the in-line sensor 428, the aspiration pump can provide waveforms delivered to the catheter that provide a positive pressure above atmospheric but below blood pressure. The positive pressures can be applied much faster and more controlled than a system utilizing a vacuum source and a vent valve. Additionally, the aspiration pump can provide fast positive pressures waveforms above blood pressure (to an attached and paired catheter restricted with thrombus) in conjunction with the in-line sensor 428 to dislodge the thrombus but prevent expelling the thrombus from the catheter. As a safety measure, the connector tubing 408 connecting the pump to the catheter may include an inline pressure release valve which can activate to release pressure prior to entering the catheter (not shown). For any of the aforementioned waveforms, the magnitude or amplitude and the frequency may be varied to achieve appropriate clot capture.

Figure 14:
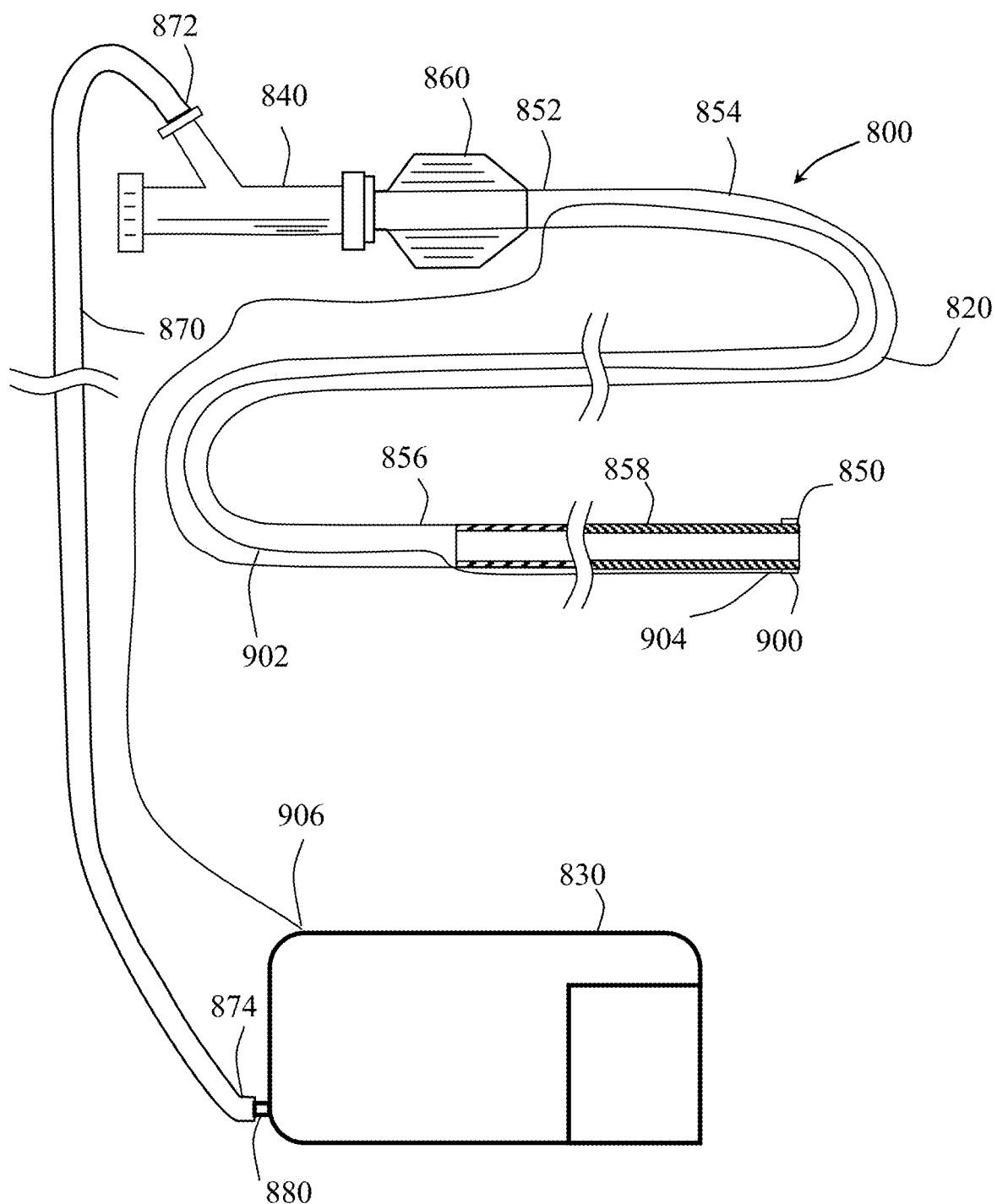
FIG. 14 is a partial cross-sectional view of a thrombectomy system including a catheter having a catheter sensor coupled to an aspiration pump.

FIG. 14 illustrates another aspect of the novel thrombectomy system. Thrombectomy system 800 includes an elongate catheter 820 and an aspiration pump 830 (embodying any of the aforementioned aspiration pump features and construction) which is coupled together using connector 840. Catheter 820 has a distal end 850, a proximal end 852 and proximal, intermediate and distal sections (854, 856 and 858 respectively) positioned between said ends. Catheter 820 includes a sensor 900 positioned in the catheter distal section 858. Preferably the sensor 900 is a pressure sensor and is capable of measuring the pressure at the distal section of the catheter, however, flow sensors may also be suitable. The output signal from the sensor 900 is transmitted through a sensor conductor 902 having a distal end 904 and a proximal end 906. Sensor conductor 902 is coupled to and extends along the length of catheter 820, where the conductor proximal end 906 may be removably coupled to the aspiration pump 830. As can be appreciated, additional sensors (not shown) can be placed at other locations along the length of the catheter (which would also coupled to the pump) to provide data to determine the pressure and or flow rate at a particular catheter locations that may correspond to a catheter obstruction or occlusion. While the sensor shown utilizes an electrical conductor, the sensor or sensors applied to the catheter may be of a wireless type that can connect to the pump wirelessly using Bluetooth, WiFi, radio frequency (RF) or other wireless communication. The information from the sensor (s) can be used by the pump to determine and subsequently apply appropriate pump output cyclic waveforms that include varying the magnitude of positive and negative pressures and/or durations (pulse widths) to aspirate thrombus during incidences where the lumen of the catheter may be obstructed. The use of these sensors (and an appropriate catheter) in conjunction with the pump would be able to provide positive pressures (above atmospheric and/or blood pressure) to the lumen of the catheter should it be obstructed without expelling material from the distal end of the catheter. Located at the proximal end of catheter 820 is a catheter hub 860 that facilitates the connection of connector 840 to the catheter. The sensor conductor uncouples from the catheter near the proximal end of the catheter where it has an appropriate length to connect to the pump while allowing unimpeded catheter access.

In order to provide an aspiration system that efficiently and effectively removes thrombus from the vasculature, the aspiration pump and catheter should be paired to account for system variables that include pump output (static and cyclic pressure waveforms, fluid volume and flow rates) and catheter variables that include catheter length, inner diameter & catheter wall compliance. While a physician may typically utilize a thrombectomy system that has a matched aspiration pump and catheter (typically from the same manufacturer), it is contemplated that some may use an unmatched system (e.g. a pump from one manufacturer and a catheter from another). These unmatched systems can lead to poor overall performance in aspirating thrombus during a procedure where the time to re-establish normal blood flow is critical. In accordance with another aspect of the novel aspiration system there is provided an aspiration pump that includes a built in "Calibration" mode. The calibration mode allows the pump to be paired with a catheter supplied from a different manufacturer to efficiently and effectively perform aspiration procedures.

In the calibration mode the primed aspiration pump operates at a known flow rate with only the pump and extension tubing. The sensor(s) on the pump along with the microprocessor controller are able to establish a baseline profile for the pump system alone. The establishment of the baseline can alternatively be performed by the manufacturer and preloaded into the memory of the pump microprocessor controller. The catheter to be paired with the aspiration pump is prepared by flushing the catheter with saline and positioning the distal end of the catheter in a container filled with saline so that the entire catheter is filled with fluid. The proximal end of the catheter is then connected to the pump extension tubing connector and the user interface on the pump is activated to start the calibration. The pump then operates under known reference conditions and takes readings from the sensor(s) to create a response profile associated with the attached catheter. The response profile associated with the catheter is then used by the microprocessor controller to adjust (as needed) the pump output cyclic pressure waveforms to pair with the catheter. This ensures that pump output waveforms are not overly dampened by the catheter, thus becoming ineffective at aspirating a thrombus. The aforementioned known reference conditions may include supplying positive pressure, negative pressure and negative and positive pressure cyclic waveforms.

In an alternative calibration mode step the catheter response profile may be obtained using a catheter that has been prepared in a different manner. After flushing and filling the catheter lumen with fluid, the distal end of the catheter is occluded using a plug tool. The plug tool may include a tapered flexible stopper portion that is inserted into the catheter lumen at its distal end and an exterior portion that removably secures the tool to the catheter. The proximal end of the catheter is then coupled to the pump extension tubing connector and the user interface on the pump is activated to start the calibration.

Many of the aforementioned systems and techniques for performing thrombectomy procedures utilize a sophisticated smart pump capable of providing both static and dynamic pressure waveforms and provide more effective thrombus removal when compared to just a static vacuum. To improve the efficacy of thrombus removal when using a static vacuum source (e.g. hospital room vacuum or a static pump) there is provided an adapter that can produce a pulsatile waveform from the static vacuum source. The pulsatile adapter connects to both the vacuum source and the thrombectomy catheter, such that when the static waveform from the source is supplied to the adapter, the adapter changes the static waveform to a pulsatile waveform and transmits it to the coupled catheter.

Figure 15A:
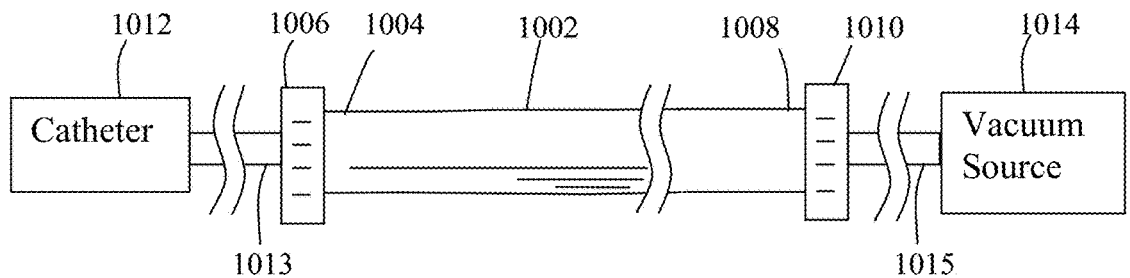
FIG. 15A is a side view of a pulsatile flow adapter coupled to a catheter and a vacuum source.
Figure 15B:
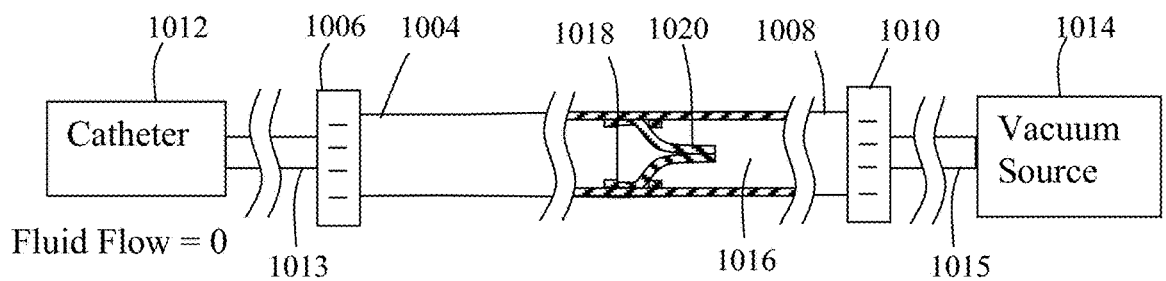
FIG. 15B is a partial sectional view of the pulsatile flow adapter in FIG. 15A at a first pressure condition.
Figure 15C:
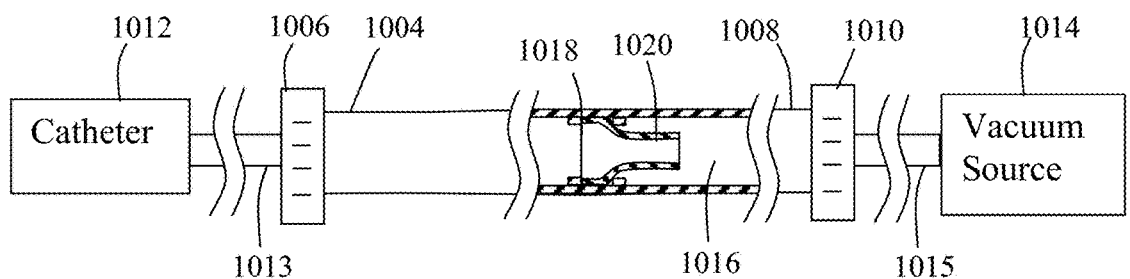
FIG. 15C is a partial sectional view of the pulsatile flow adapter in FIG. 15A at a second pressure condition.
Figure 15D:
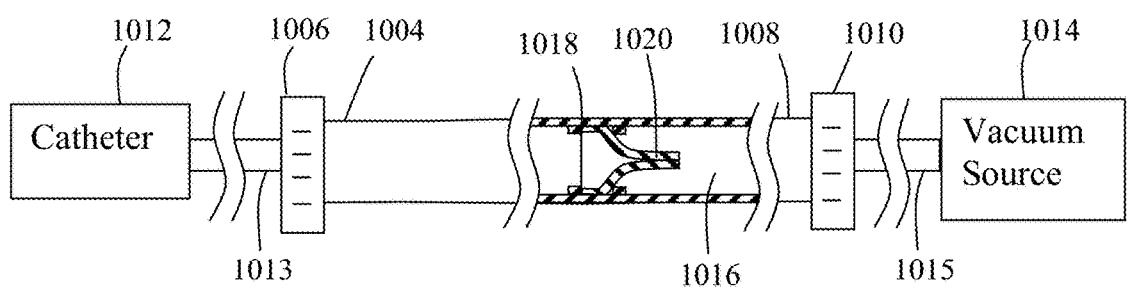
FIG. 15D is a partial sectional view of the pulsatile flow adapter in FIG. 15A at a third pressure condition.

An embodiment of a pulsatile adapter is illustrated in FIG. 15A. The pulsatile adapter 1000 generally takes the form of a tubular housing member 1002 having a first end 1004 and connector 1006, a second end 1008 and connector 1010. First end 1004 is typically coupled to a catheter 1012 via tubing 1013 while second end 1008 is coupled to a vacuum source 1014 via tubing 1015. FIG. 15B shows a partially sectioned view of tubular housing member 1002 that includes a lumen 1016. Within lumen 1016, positioned between the first end 1004 and the second end 1008 there is a valve assembly 1018 containing a resilient valve 1020. Valve 1020 of the adapter is resiliently biased to a closed configuration preventing flow fluid flow through the lumen 1016 between the ends of the adapter. The valve 1020 preferably takes the form of a slit valve, duck bill or cross slit valve, however, other types of valves may also be suitable. The design of valve 1020 is such that it has the ability to move to an open configuration (thus allowing fluid flow through the lumen 1016 of the housing member between the ends of the adapter) when an applied pressure to one side of the valve exceeds a valve opening pressure. For clarity, since vacuums are associated with negative pressure, when the absolute value of the applied pressure, $P_{APP}$ exceeds the absolute value of the valve opening pressure, $P_{VOpen}$, the valve moves from the closed configuration to the open configuration. As illustrated in FIG. 15C, when the absolute value of $P_{APP}$ from vacuum source 1014 exceeds the absolute value of $P_{VOpen}$ the valve 1020 opens, allowing fluid flow through the lumen 1016 between the adapter ends. If the fluid flow through the lumen 1016 reaches a level such that the pressure in the lumen 1016 region between the valve 1020 and vacuum source 1014 decreases, effectively decreasing $P_{APP}$ below $P_{VOpen}$, the valve 1020 will move to its biased closed configuration as shown in FIG. 15D. As the absolute value of the pressure in the lumen 1016 region increases between the closed valve 1020 and the vacuum source 1014, and the applied pressure, $P_{APP}$ effectively exceeds $P_{VOpen}$ and the valve opens again. This repeating process creates a pulsatile pressure waveform through the adapter end opposite to the adapter end connected to the static pressure source. In this case, when the first end 1004 of the adapter 1000 is connected to a catheter 1012, the repeating process transmits a pulsatile pressure waveform to the catheter 1012 from the pressure applied from the static vacuum source 1014. As can be appreciated, the pulsatile adapter may also be used with a non-static varying pressure source (vacuum source) to modify the pressure wave that would be applied to the catheter.

Figure 16A:
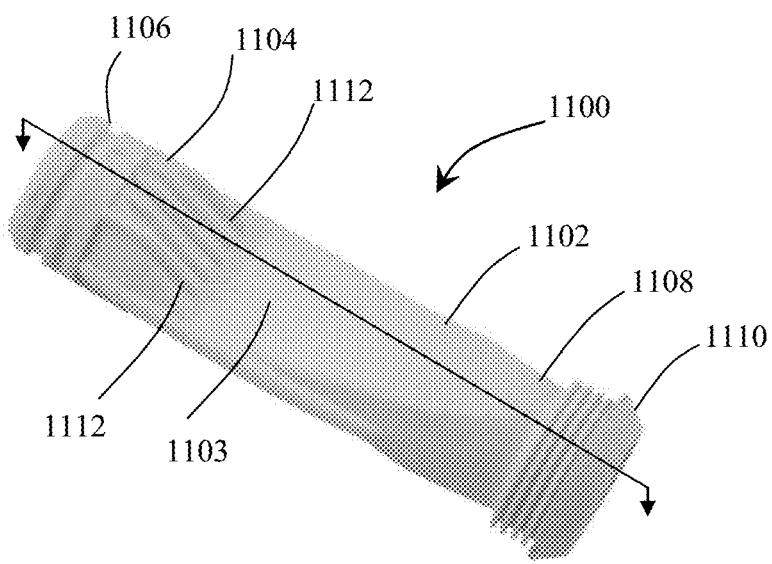
FIG. 16A. is a perspective view of an integrally formed pulsatile flow adapter.
Figure 16B:
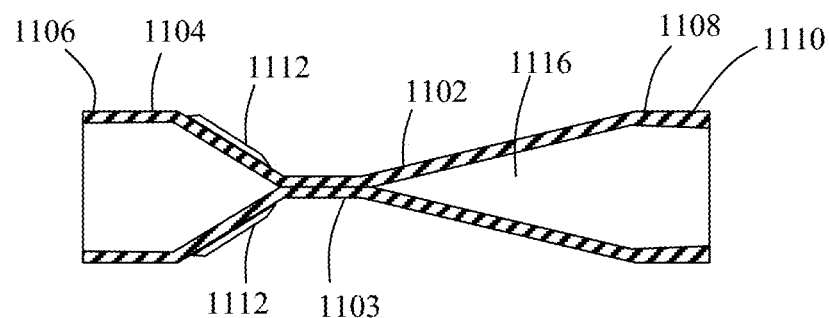
FIG. 16B. is a partial sectional view of an integrally formed pulsatile flow adapter with a valve in the normally biased closed configuration.
Figure 16C:
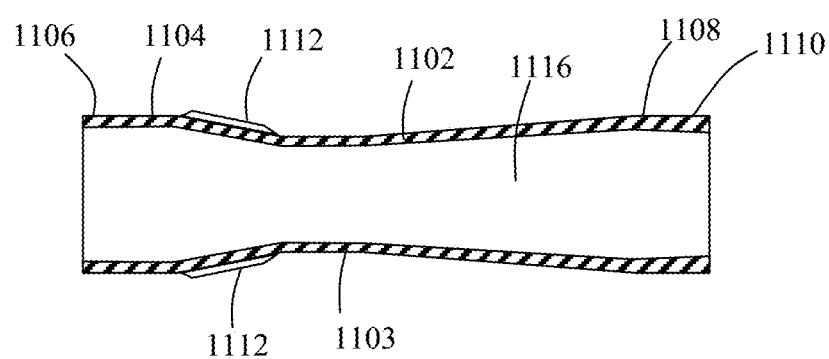
FIG. 16C. is a partial sectional view of an integrally formed pulsatile flow adapter with a valve show in the open configuration.

FIG. 16A illustrates an example of a single piece, pulsatile adapter 1100 where the housing 1102 and valve assembly 1103 are integrally formed and include first end 1104 having connector 1106 and second end 1108 having connector 1110 where the connectors 1106 and 1110 are adapted to be connected to a catheter and a pressure source, respectively, with appropriate coupler fittings. The integrally formed ends may be configured to connect directly to a catheter and or pressure source if desired. FIG. 16B shows the cross sectioned integrally formed pulsatile adapter 1100, formed of a resilient material and the valve assembly 1103 resiliently biased in closed configuration that prevents fluid flow through lumen 1116 between ends 1104 and 1108. Valve assembly 1103 includes a plurality of reinforcing members 1112 which aid in maintaining the valve assembly in a closed configuration. FIG. 16C shows a cross section of integrally formed pulsatile adapter 1100 when valve assembly 1103 is in an open configuration where fluid flow between ends 1104 and 1108 through lumen 1116 is enabled. As can be appreciated, the integrally formed pulsatile adapter must flex considerably to open from its closed configuration and must be resilient to return to the biased closed configuration. Suitable materials for the integrally formed adapter include silicones, urethanes, rubber and other flexible resilient thermoset or thermoplastic elastomers. Integrally formed pulsatile adapter 1100 functions similarly to previously described pulsatile adapter in that when the first end 1104 is coupled to a catheter and the second end 1108 is coupled to a static vacuum source and the pressure in the lumen region between the valve assembly 1103 and the vacuum source exceeds a valve assembly opening pressure the valve assembly 1103 moves from the biased closed configuration to an open configuration. Conversely, when the pressure in lumen region between the valve assembly and the vacuum source decreases below the valve assembly opening pressure the valve assembly reverts to the biased closed configuration. This repeating process creates a pulsatile waveform that is applied to the catheter from the static source.

Since the magnitude of the fluid flow between the valve and the static pressure source is related to the effective pressure in the region between the valve and the adapter end connected to the static pressure source, there may be a need to control the fluid flow rate. For instance, if the applied pressure is sufficiently high and the fluid flow is exceedingly low, then the pressure in the region between the valve and static source may effectively exceed $P_{VOpen}$ causing the valve to remain in an open configuration. Another embodiment of the pulsatile adapter can remedy this situation by configuring the adapter to include a secondary valve (preferably adjustable) positioned between the primary valve and the adapter end connected to the pressure source.

Figure 17A:
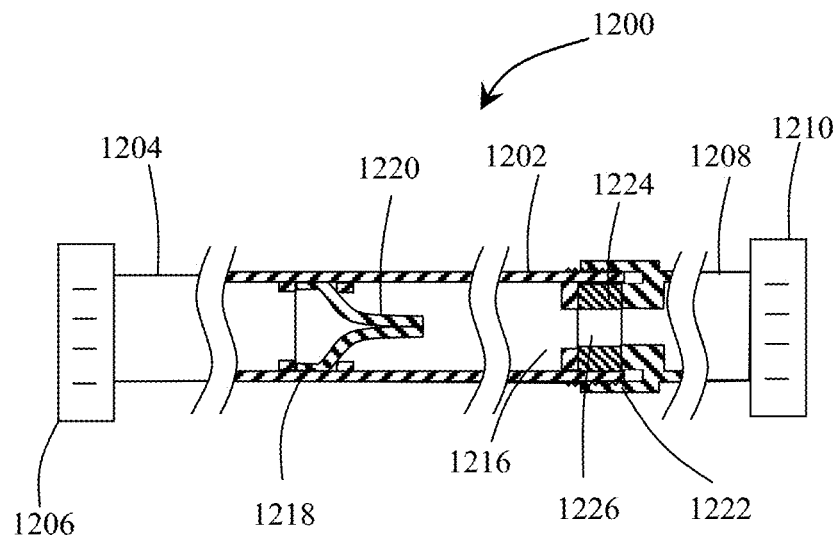
FIG. 17A is a partial side view of a pulsatile flow adapter including a secondary adjustable valve.
Figure 17B:
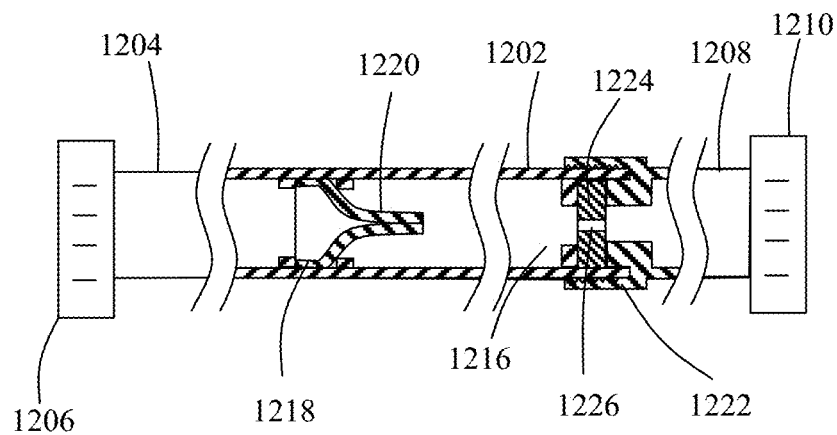
FIG. 17B is a partial side view of a pulsatile flow adapter including a secondary adjustable valve that is partially closed.

FIG. 17A shows a partially sectioned view of pulsatile adapter 1200 that generally takes the form of a tubular housing member 1202 having a first end 1204 and connector 1206, a second end 1208 and connector 1210. First end 1204 is typically coupled to a catheter via tubing and connector 1206 while second end 1208 is coupled to a vacuum source via tubing and connector 1210. Tubular housing member 1202 includes a through lumen 1216. Within the lumen 1016, between the first end 1204 and second end 1208 there is a first valve assembly 1218 containing a resilient first valve 1220. First valve 1220 of the adapter is resiliently biased to a closed configuration preventing flow fluid flow through the lumen 1216 between the ends of the adapter. The valve 1220 preferably takes the form of a slit valve, duck bill or cross slit valve, however, other types of valves may also be suitable. The design of valve 1220 is such that it has the ability to move to an open configuration (thus allowing fluid flow through the lumen 1216 of the housing member between the ends of the adapter) when an applied pressure to one side of the valve exceeds a valve opening pressure. Positioned within lumen 1216 between first valve assembly 1218 and second end 1208 is a second valve assembly 1222 that includes a second valve 1224 having a valve orifice 1226 with an adjustable orifice diameter. Second valve 1224 takes the form of a thick walled cylinder having valve orifice 1226 with a pre-set diameter. Second valve 1224 is preferably formed from a resilient material that includes materials such as silicones, rubbers, urethanes and other elastomeric materials. Second valve assembly 1222 is of a rotational type valve assembly in which rotation of the assembly in a first direction causes second valve 1224 to be compressed thereby reducing the diameter of valve orifice 1226, as shown in FIG. 17B. When second valve 1224 is in the compressed configuration and second valve assembly 1222 is rotated in a second direction, opposite from the first direction, second valve 1224 becomes uncompressed and the resilient nature of the valve material allows the diameter of valve orifice 1226 to increase up to the maximum pre-set diameter. By rotating second valve assembly 1222 in first or second directions (compressing or decompressing second valve 1224) the diameter of valve orifice 1226 may be adjusted. When coupled to a catheter and a vacuum source the pulsatile adapter 1200 operates similarly to those previously described herein, however, the second valve assembly 1222 has the effect of adding a control to the rate of pressure change in the region of the adapter between the first and second valve assemblies (by controlling the rate of volume change of the region during fluid flow). For instance, should the connected static vacuum have a fluid flow rate that causes the first valve to remain in a constantly open state, the second valve assembly may be rotated to decrease the valve orifice diameter allowing the first valve to close initiating a pulsatile wave form.

Novel devices, systems and methods have been disclosed to perform thrombectomy procedures within the vessel of a mammal. Although preferred embodiments have been described, it should be understood that various modifications including the substitution of elements or components which perform substantially the same function in the same way to achieve substantially the same result may be made by those skilled in the art without departing from the scope of the claims which follow.

What is claimed is:

1. A method of removing thrombus from a vessel using a thrombus removal system comprising:
    providing an elongate catheter having proximal and distal ends and an inner diameter;
    providing an aspiration pump having a sensor, an aspiration container, a non-dampening extension tube and a microprocessor controller, said aspiration pump further having an operable mode that generates a cyclic pressure waveform such that when said aspiration pump is coupled to said catheter positioned within a vessel adjacent a thrombus and operated, said pump controllably cycles supplying negative pressure to said catheter to aspirate a thrombus through the catheter to the pump aspiration container;

positioning the distal end of the catheter within a vessel lumen adjacent a thrombus;

coupling the aspiration pump extension tube to the catheter;

operating the aspiration pump to provide a pressure waveform which includes providing cyclic negative and positive pressure to a lumen of the catheter thereby suctioning thrombus through the catheter lumen and into the aspiration container.

2. The method of removing thrombus according to claim 1, including coupling the catheter to said aspiration pump where said aspiration pump includes a calibration mode, initiating said calibration mode such that the aspiration pump performs a calibration with said catheter and uncoupling said catheter from said aspiration pump prior to positioning the distal end of the catheter within a vessel lumen adjacent a thrombus.

3. The method of removing thrombus according to claim 1, wherein operating the aspiration pump includes initiating a first embedded program in said microprocessor controller whereby said aspiration pump provides steady vacuum pressure until said sensor detects pressure at a first preset limit and a restricted catheter fluid flow state.

4. The method of removing thrombus according to claim 3, wherein upon when said sensor detects a pressure reaching said first preset limit, said operating the aspiration pump includes terminating said first embedded program and initiating a second embedded program in said microprocessor controller whereby said aspiration pump provides a series of cyclic pressure waveforms until said sensor detects a pressure at a second preset limit.

5. The method of removing thrombus according to claim 4, wherein said series of cyclic pressure waveforms range from low amplitude and low frequency to high amplitude and high frequency until the sensor detects an unrestricted catheter fluid flow state.

6. A method of removing thrombus from a vessel using a thrombus removal system comprising:

providing an elongate catheter having proximal and distal ends and an inner diameter;

providing an aspiration pump having a sensor, an aspiration container, a non-dampening extension tube and a microprocessor controller, said aspiration pump further having an operable mode that generates a cyclic pressure waveform such that when said aspiration pump is coupled to said catheter positioned within a vessel adjacent a thrombus and operated, said pump controllably cycles supplying negative pressure to said catheter to aspirate a thrombus through the catheter to the pump aspiration container;

positioning the distal end of the catheter within a vessel lumen adjacent a thrombus;

coupling the aspiration pump extension tube to the catheter;

operating the aspiration pump to provide a pressure waveform to a lumen of the catheter thereby suctioning thrombus through the catheter lumen and into the aspiration container including initiating a first embedded program in said microprocessor controller whereby said aspiration pump provides steady vacuum pressure until said sensor detects pressure at a first preset limit and a restricted catheter fluid flow state.

7. The method of removing thrombus according to claim 6, wherein upon when said sensor detects a pressure reaching said first preset limit, said operating the aspiration pump includes terminating said first embedded program and initiating a second embedded program in said microprocessor controller whereby said aspiration pump provides a series of cyclic pressure waveforms until said sensor detects a pressure at a second preset limit.

8. The method of removing thrombus according to claim 7, wherein initiating a second embedded program is initiated by said aspiration pump.

9. The method of removing thrombus according to claim 7, wherein said series of cyclic pressure waveforms range from low amplitude and low frequency to high amplitude and high frequency until the sensor detects an unrestricted catheter fluid flow state.

10. The method of removing thrombus according to claim 6, wherein upon when said sensor detects a pressure reaching said first preset limit, said operating the aspiration pump includes terminating said first embedded program and initiating a second embedded program in said microprocessor controller whereby said aspiration pump provides a series of cyclic pressure waveforms until said sensor detects an unrestricted catheter fluid flow state.

11. The method of removing thrombus according to claim 10, wherein initiating a second embedded program is initiated by said aspiration pump.

12. The method of removing thrombus according to claim 10, wherein said series of cyclic pressure waveforms range from low amplitude and low frequency to high amplitude and high frequency until the sensor detects an unrestricted catheter fluid flow state.

13. The method of removing thrombus according to claim 6, including coupling the catheter to said aspiration pump where said aspiration pump includes a calibration mode, initiating said calibration mode such that the aspiration pump performs a calibration with said catheter and uncoupling said catheter from said aspiration pump prior to positioning the distal end of the catheter within a vessel lumen adjacent a thrombus.

14. A method of removing thrombus from a vessel using a thrombus removal system comprising:

providing an elongate catheter having proximal and distal ends and an inner diameter;

providing an aspiration pump having a sensor, an aspiration container, a non-dampening extension tube and a microprocessor controller, said aspiration pump further having an operable mode that generates a cyclic pressure waveform such that when said aspiration pump is coupled to said catheter positioned within a vessel adjacent a thrombus and operated, said pump controllably cycles supplying negative pressure to said catheter to aspirate a thrombus through the catheter to the pump aspiration container;

positioning the distal end of the catheter within a vessel lumen adjacent a thrombus;

coupling the aspiration pump extension tube to the catheter;

operating the aspiration pump to provide a pressure waveform to a lumen of the catheter thereby suctioning thrombus through the catheter lumen and into the aspiration container including terminating said provided pressure waveform if said sensor does not detect a pressure at a preset limit within 30 seconds.

15. The method of removing thrombus according to claim 14, wherein operating the aspiration pump includes initiating a first embedded program in said microprocessor controller whereby said aspiration pump provides steady vacuum pressure until said sensor detects pressure at a first preset limit and a restricted catheter fluid flow state.

16. The method of removing thrombus according to claim 15, wherein upon when said sensor detects a pressure reaching said first preset limit, said operating the aspiration pump includes terminating said first embedded program and initiating a second embedded program in said microprocessor controller whereby said aspiration pump provides a series of cyclic pressure waveforms until said sensor detects a pressure at a second preset limit.

17. The method of removing thrombus according to claim 16, wherein said series of cyclic pressure waveforms range from low amplitude and low frequency to high amplitude and high frequency until the sensor detects an unrestricted catheter fluid flow state.

18. The method of removing thrombus according to claim 14, including coupling the catheter to said aspiration pump where said aspiration pump includes a calibration mode, initiating said calibration mode such that the aspiration pump performs a calibration with said catheter and uncoupling said catheter from said aspiration pump prior to positioning the distal end of the catheter within a vessel lumen adjacent a thrombus.

* * * * *